US007915219B2

(12) United States Patent
Mochly-Rosen et al.

(10) Patent No.: US 7,915,219 B2
(45) Date of Patent: *Mar. 29, 2011

(54) METHOD FOR REDUCING CENTRAL NERVOUS SYSTEM TISSUE OR CELL DAMAGE IN A SUBJECT DUE TO STROKE

(75) Inventors: Daria Mochly-Rosen, Menlo Park, CA (US); Leon E. Chen, Belmont, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 48 days.

This patent is subject to a terminal disclaimer.

(21) Appl. No.: 11/838,732

(22) Filed: Aug. 14, 2007

(65) Prior Publication Data

US 2009/0075901 A1  Mar. 19, 2009

Related U.S. Application Data

(60) Continuation of application No. 10/843,731, filed on May 12, 2004, now Pat. No. 7,745,388, which is a division of application No. 10/007,761, filed on Nov. 9, 2001, now Pat. No. 6,855,693.

(60) Provisional application No. 60/262,060, filed on Jan. 18, 2001.

(51) Int. Cl.
*A61K 38/00* (2006.01)
*C07K 7/00* (2006.01)
(52) U.S. Cl. .......................................... 514/2; 530/300
(58) Field of Classification Search ........................ None
See application file for complete search history.

(56) References Cited

U.S. PATENT DOCUMENTS

| | | |
|---|---|---|
| 4,708,871 A | 11/1987 | Geysen |
| 5,776,716 A | 7/1998 | Napolitano et al. |
| 5,783,405 A | 7/1998 | Mochly-Rosen et al. |
| 6,165,977 A | 12/2000 | Mochly-Rosen |
| 6,664,040 B2 | 12/2003 | Sherman et al. |
| 6,855,693 B2 | 2/2005 | Mochly-Rosen et al. |
| 7,265,092 B2 | 9/2007 | Li |
| 7,563,772 B2 | 7/2009 | Mochly-Rosen et al. |
| 2004/0204364 A1 | 10/2004 | Mochly-Rosen et al. |
| 2008/0075706 A1 | 3/2008 | Li |
| 2009/0062208 A1 | 3/2009 | Mochly-Rosen et al. |
| 2009/0075901 A1 | 3/2009 | Mochly-Rosen et al. |
| 2009/0186814 A1 | 7/2009 | Ikeno et al. |
| 2009/0192089 A1 | 7/2009 | Mochly-Rosen et al. |

FOREIGN PATENT DOCUMENTS

| WO | WO-97/14038 | 4/1997 |
|---|---|---|
| WO | WO-2009/029678 | 3/2009 |

OTHER PUBLICATIONS

Del Zoppo, Clinical trials in acute stroke: why have they not been successful? Neurology. Sep. 1998;51(3 Suppl 3):559-61.*

USPTO in house BLAST alignment; Seq ID No. 4 vs human PKCdelta (NP_006245.2). Performed Aug. 4, 2010.*
Daria Mochly-Rosen, List of peptides provided for experimental use sent to Lobo Lab, University of California, San Francisco, San Francisco, California, US. Feb. 11, 1998.
Che-Hong Chen, List of peptides provided for expermiental use sent to Dr. Sailen Barik, Department of Biochemistry and Molecular Biology, University of Southern Alabama, Mobile, Alabama, US Mar. 19, 1998.
Che-Hong Chen, List of peptides provided for expermiental use sent to Dr. Derek Miles Yellon, Hatter Institute for Cardiovascular Studies, Department of Academic and Clincial Cardiology, University of College Hospital and Medical School, London, UK Jun. 25, 1998.
Che-Hong Chen, List of peptides provided for expermiental use sent to Dr. Derek Miles Yellon, Hatter Institute for Cardiovascular Studies, Department of Academic and Clincial Cardiology, University of College Hospital and Medical School, London, UK Oct. 14, 1998.
Email to Dr. Dr. Derek Miles Yellon, Hatter Institute for Cardiovascular Studies, Department of Academic and Clincial Cardiology, University of College Hospital and Medical School, London, UK Oct. 14, 1998.
Email to Dr. Dr. Derek Miles Yellon, Hatter Institute for Cardiovascular Studies, Department of Academic and Clincial Cardiology, University of College Hospital and Medical School, London, UK Aug. 9, 1998.
Che-Hong Chen, List of peptides provided for expermiental use sent to Dr. Fiorenzo Battaini, Institute of Pharmacological Sciences, University of Milano Milano, IT, Oct. 15, 1998.
Email from Fiorenzo Battaini, Aug. 14, 1998.
Fiorenzo Battaini, Letter outling project, Aug. 14, 1998.
Che-Hong Chen, List of peptides provided for expermiental use sent to Dr. Ashwani Malhotra, Cardiovascular Research Institute, New York Medical Colloge, Valhalla, New York, US. Oct. 16, 1998.
Ashwanu Malhotra, List of peptides provided for expermiental use sent to Dr. Ashwani Malhotra, Cardiovascular Research Institute, New York Medical College, Valhalla, New York, US, Oct. 16, 1998.
Che-Hong Chen, List of peptides provided for expermiental use sent to Dr. Naoaki Saito, Laboratory of Molecular Pharmacology, Biosignal Research Center, Kobe University, Kobe, JP, Oct. 15, 1998.
Naoaki Saito, Email requesting peptidesList of peptides provided for expermiental use sent to Dr. Naoaki Saito, Laboratory of Molecular Pharmacology, Biosignal Research Center, Kobe University, Kobe, JP, Oct. 15, 1998.
Che-Hong Chen, List of peptides provided for expermiental use sent to Dr. Mohamed Boutjdir, Department of Cardiology, VA Medical Center, Brooklyn, New York, US, Aug. 14, 1998.
Che-Hong Chen, List of peptides provided for expermiental use sent to Drs. Rik Derynck and Huizhou Fan, Department of Growth and Development, University of California, San Francisco, San Franciso, California, US, Oct. 27, 1998.
Che-Hong Chen, List of peptides provided for expermiental use sent to Drs. Rik Derynck and Huizhou Fan, Department of Growth and Development, University of California, San Francisco, San Franciso, California, US, Oct. 26, 1998.

(Continued)

*Primary Examiner* — Sheridan Swope
(74) *Attorney, Agent, or Firm* — Morrison & Foerster LLP

(57) ABSTRACT

Peptides able to inhibit or activate the translocation or function of δPKC are identified. Administration of the peptides for protection or enhancement of cell damage due to ischemia is described. Therapeutic methods to reduce damage to cells or to enhance damage to cells due to ischemia are also described, as well as methods for screening test compounds for δPKC-selective agonists and antagonists.

14 Claims, 11 Drawing Sheets

OTHER PUBLICATIONS

Purchase Order for PKC peptides, Department of Growth and Development, University of California, San Francisco, San Francisco, California, US. Oct. 26, 1998.

Daria Mochly-Rosen, Material Transfer Agreement and List of peptides provided for expermiental use sent to Drs. Rik Derynck and Huizhou Fan, Department of Growth and Development, University of California, San Francisco, San Francisco, California, US, Oct. 26, 1998.

Daria Mochly-Rosen, Email regarding request for peptides for expermiental use from Drs. Rik Derynck and Huizhou Fan, Department of Growth and Development, University of California, San Francisco, San Francisco, California, US, Sep. 11, 1998.

Che-Hong Chen, List of peptides provided for expermiental use sent to Dr. Marsha Rosner, Department of Pharmacological and Physiological Sciences, University of Chicago, Chicago, Illinois, US, Nov. 17, 1998.

Daria Mochly-Rosen, Email regarding request for peptides for expermiental use from Dr. Marsha Rosner, Oct. 27, 1998.

Che-Hong Chen, List of peptides provided for expermiental use sent to Dr. John Hayslett, Yale School of Medicine, New Haven, Conneticut, US, Dec. 14, 1998.

John Hayslett, Letter of Dr. Mochly-Rosen requesting peptides, Oct. 28, 1998.

Che-Hong Chen, List of peptides provided for expermiental use sent to Dr. Guang S. Liu, Department of Physiology, University of South Alabama, Mobile, Alabama, US, Nov. 23, 1998.

Daria Mochly-Rosen, signed Material Transfer Agreement with Dr. Steven Pelech, Department of Medicine, University of British Columbia, Vancouver, B.C., CA, Feb. 10, 1999.

Daria Mochly-Rosen, Email to Dr. Steven Pelech regarding peptides, Feb. 8, 1999.

Daria Mochly-Rosen, Material Transfer Agreement to Dr. Pedro A. Jose, Georgetown University Hospital, Washington, D.C., US, Feb. 17, 1999.

Che-Hong Chen, List of peptides provided for expermiental use sent to Dr. Rafael Nesher, Department of Endocrinology, University of South Alabama, Mobile, Alabama, US, Feb. 10, 1999.

Daria Mochly-Rosen, Email to Dr. Rafael Nesher regarding peptides, Feb. 8, 1999.

Che-Hong Chen, List of peptides provided for expermiental use sent to Dr. Chaya Brodie, Faculty of Life Sciences, Bar-Ilan University, Ramat-Gan, Israel, Mar. 11, 1999.

Email traffic between Drs. Mochly-Rosen and Brodie regarding peptides.

Daria Mochly-Rosen, Material Transfer Agreement to Dr. Chaya Brodie, Faculty of Life Sciences, Bar-Ilan University, Ramat-Gan, Israel, Mar. 11, 1999.

Che-Hong Chen, List of peptides provided for expermiental use sent to Dr. Mireia Gomez-Angelats, National Institute of Environmental Health Sciences, RTP, NC, US, Jul. 13, 1999.

Email traffic between Drs. Mochly-Rosen and Gomez-Angelats regarding peptides, Jun. 18, 1999.

Daria Mochly-Rosen, Material Transfer Agreement to Dr. Cindy Miranti, Department of Cell Biology, Harvard Medical School, Boston, Massachusetts, US, Nov. 30, 1999.

Daria Mochly-Rosen, Material Transfer Agreement to Dr. Alexei Kourakine, Department of Cell Biology, Harvard Medical School, Boston, Massachusetts, US, Nov. 30, 1999.

Che-Hong Chen, List of peptides provided for expermiental use sent to Dr. Karen M. Ridge, Northwestern University, Chicago, Illinois, Apr. 4, 2000.

Email traffic between Drs. Mochly-Rosen and Yuri Volkov, SPD Research Laboratory, The Trinity Centre for Health Sciences, St. James Hospital, Dublin, Ireland, Jun. 18, 1999.

Che-Hong Chen, Material Transfer Agreement and supporting documents to Dr. Steve Black, Department of Pediatrics, University of California, San Francisco, California, US, Sep. 3, 1998.

Daria Mochly-Rosen, Material Transfer Agreement to Dr. Umberto Kucich, School of Dental Medicine, Department of Anatomy and Histology, Philadelphia, PA, US, Nov. 6, 1998.

Che-Hong Chen, List of peptides provided for expermiental use sent to Dr. Umberto Kucich, School of Dental Medicine, Department of Anatomy and Histology, Philadelphia, PA, US, Nov. 12, 1998.

Daria Mochly-Rosen, Material Transfer Agreement to Dr. Victor Fomin, Department of OB-GYN, Indiana University, Indianapolis, Indiana, US, Nov. 18, 1998.

Che-Hong Chen, List of peptides provided for expermiental use sent to Dr. Victor Fomin, Department of OB-GYN, Indiana University, Indianapolis, Indiana, US, Nov. 19, 1998.

Daria Mochly-Rosen, Material Transfer Agreement to Dr. Tish Murphy, NIEHS, NIH, Research Triangle Park, NC, US, Dec. 15, 1998.

Daria Mochly-Rosen, Material Transfer Agreement to Dr. Barbara Cordell, Scios Corporated, Sunnyvale, CA, US, Dec. 15, 1998.

Daria Mochly-Rosen, Material Transfer Agreement to Dr. Yuri Volkov, SPD Research Laboratory, The Trinity Centre for Health Sciences, St. James Hospital, Dublin, Ireland, Dec. 15, 1998.

Daria Mochly-Rosen, Material Transfer Agreement to Dr. Arshad Rahman, Department of Pharmacology, University of Illinois, UA, Dec. 15, 1998.

Daria Mochly-Rosen, Material Transfer Agreement to Dr. Andrew P. Bradford, Department of Obstetrics & Gynecology, University of Colorado Health Science, Colorado, US, Dec. 15, 1998.

Daria Mochly-Rosen, Email to Dr. Andrew P. Bradford, Department of Obstetrics & Gynecology, University of Colorado Health Science, Colorado, US, Dec. 4, 1998.

Babu Padanilam, Renal Division, Washington University Medical School, St. Louis, MO, US, Email traffic with Dr. Daria Mochly-Rosen, Oct. 15, 1998.

Daria Mochly-Rosen, Material Transfer Agreement to Dr. Babu Padanilam, , Renal Division, Washington University Medical School, St. Louis, MO, US, Oct. 29, 1998.

Che-Hong Chen, List of peptides provided for expermiental use sent to Dr. Babu Padanilam, , Renal Division, Washington University Medical School, St. Louis, MO, US, Oct. 29, 1998.

Che-Hong Chen, List of peptides provided for expermiental use sent to Dr. Steve Black, Department of Pediatrics, University of California, San Francisco, California, US, Sep. 3, 1998.

Che-Hong Chen, correspondence with Dr. Yuri Volkov regarding peptides provided for expermiental use, California, US, Jan. 25, 1999.

Andrew P. Bradford, Correspondence regarding peptides provided for expermiental use, Colorado, US, Jan. 27, 1999.

Mita Das, Email traffic requesting peptides for experimental use, Denver, Colorado, US, Jan. 7, 1999.

Daria Mochly-Rosen, Material Transfer Agreement to Dr. Mita Das, CVP and Developmental Lung Biology Labs, University of Colorado, Health Sciences Center, Denver, CO, US, Jan. 11, 1999.

Eric Nelson, Email traffic regarding request for peptides for experimental use, Department of Pharmacology, University of Colorado, Denver, CO, Jan. 11, 1999.

Che-Hong Chen, List of peptides provided for expermiental use sent to Dr. Eric Nelson, Department of Pharmacology, University of Colorado, Denver, CO, US, Jan. 14, 1999.

Eric Nelson, correspondence regarding experimental data produced from requested peptides, Department of Pharmacology, University of Colorado, Denver, CO, US, Oct. 1, 1999.

Umberto Kucich, School of Dental Medicine, Department of Anatomy and Histology, Philadelphia, PA, US, Email traffic regarding peptide request, Nov. 12, 1998.

Daria Mochly-Rosen, Material Transfer Agreement to Dr. Johannes W. Hell, Department of Pharmacology, University of Wisconsin Medical School, Madison, WI, US, Sep. 22, 1999.

Johannes W. Hell, Department of Pharmacology, University of Wisconsin Medical School, Madison, WI, US, Correspondence regarding peptides and experimental program, Sep. 23, 1999.

Yukitaka Shizukadua, Section of Cardiology, University of Illinois at Chicago, Illinois, Email correspondence requesting peptides, Oct. 29, 1999.

Che-Hong Chen, Material Transfer Agreement and list of peptides provided for expermiental use sent to Dr. Yukitaka Shizukadua, Section of Cardiology, University of Illinois at Chicago, Illinois, US, Jan. 14, 1999.

Daria Mochly-Rosen, Material Transfer Agreement to Dr. Hesam Dehghani, Department of Pharmacology, University of Wisconsin Medical School, Madison, WI, US, Nov. 8, 1999.

Daria Mochly-Rosen, Email correspondenc with Dr. Jesus Garcia, Department of Physiology and Biophysics, Chicago, Illinois, US, requesting peptides, Jan. 26, 2000.

Daria Mochly-Rosen, Material Transfer Agreement to Dr. Jesus Garcia, Department of Physiology and Biophysics, Chicago, Illinois, US, Mar. 8, 2000.

Daria Mochly-Rosen, Material Transfer Agreement to Dr. Clive M. Baumgarten, Medical Collage of Virginia, Virginia Commonwealth University, Richmond, Virginia, US, Feb. 3, 2000.

Wells, Biochemistry (1990) 29(37):8509-8517.

Armstrong, S., J. M. Downey, et al. (1994). "Preconditioning of isolated rabbit cardiomyocytes: induction by metabolic stress and blockade by the adenosine antagonist SPT and calphostin C, a protein kinase C inhibitor." *Cardiovasc Res* 28(1): 72-7.

Baier et al., J. Biol. Chem. (1993) 268:4997-5004.

Brew, E. C., M. B. Mitchell, et al. (1995). "Role of bradykinin in cardiac functional protection after global ischemia-reperfusion in rat heart." *Am J Physiol* 269(4 Pt 2): H1370-8.

Colbert et al., J. Clin. Invest. (1997) 100:1958.

Csukai et al., (1995) 9$^{th}$ International Conference on Second Messengers and Phosphoproteins ,112.

Csukai, M., C. H. Chen, et al. (1997). "The coatomer protein beta'-COP, a selective binding protein (RACK) for protein kinase Cepsilon." *J Biol Chem* 272(46): 29200-6.

Disatnik, M. H., G. Buraggi, et al. (1994). "Localization of protein kinase C isozymes in cardiac myocytes." *Exp Cell Res* 210(2): 287-97.

Dorn, G. W., 2nd, M. C. Souroujon, et al. (1999). "Sustained in vivo cardiac protection by a rationally designed peptide that causes epsilon protein kinase C translocation." *Proc Natl Acad Sci U S A* 96(22): 12798-803.

Gray, M. O., J. S. Karliner, et al. (1997). "A selective epsilon-protein kinase C antagonist inhibits protection of cardiac myocytes from hypoxia-induced cell death." *J Biol Chem* 272(49): 30945-51.

Guo et al., Am. J. Physiol. (1998) 275:H1375-H1387.

Hu, K. and S. Nattel (1995). "Mechanisms of ischemic preconditioning in rat hearts. Involvement of alpha 1B-adrenoceptors, pertussis toxin-sensitive G proteins, and protein kinase C." *Circulation* 92(8): 2259-65.

Johnson, J. A. and D. Mochly-Rosen (1995). "Inhibition of the spontaneous rate of contraction of neonatal cardiac myocytes by protein kinase C isozymes. A putative role for the epsilon isozyme." *Circ Res* 76(4): 654-63.

Johnson, J. A., M. O. Gray, et al. (1996). "An improved permeabilization protocol for the introduction of peptides into cardiac myocytes. Application to protein kinase C research." *Circ Res* 79(6): 1086-99.

Liu, Y., A. Tsuchida, et al. (1995). "Pretreatment with angiotensin II activates protein kinase C and limits myocardial infarction in isolated rabbit hearts." *J Mol Cell Cardiol* 27(3): 883-92.

Mackay, K. and D. Mochly-Rosen (1999). "An inhibitor of p38 mitogen-activated protein kinase protects neonatal cardiac myocytes from ischemia." *J Biol Chem* 274(10): 6272-9.

Maier et al., Stroke (1998) 29:2171-2180.

Mitchell et al., Circulation (1993) 88:1633.

Mitchell, M. B., X. Meng, et al. (1995). "Preconditioning of isolated rat heart is mediated by protein kinase C." *Circ Res* 76(1): 73-81.

Mitchell, D. J., D. T. Kim, et al. (2000). "Polyarginine enters cells more efficiently than other polycationic homopolymers." *J Pept Res* 56(5): 318-25.

Mochly-Rosen, D., C. J. Henrich, et al. (1990). "A protein kinase C isozyme is translocated to cytoskeletal elements on activation." *Cell Regul* 1(9): 693-706.

Mochly-Rosen, D., H. Khaner, et al. (1991). "Intracellular receptors for activated protein kinase C. Identification of a binding site for the enzyme." *J Biol Chem* 266(23): 14866-8.

Mochly-Rosen, D., G. Wu, et al. (2000). "Cardiotrophic effects of protein kinase C epsilon: analysis by in vivo modulation of PKCepsilon translocation." *Circ Res* 86(11): 1173-9.

Murry, C. E., R. B. Jennings, et al. (1986). "Preconditioning with ischemia: a delay of lethal cell injury in ischemic myocardium." *Circulation* 74(5): 1124-36.

Osada et al., Molec. Cell. Biol. (1992) 12:3930.

Papadopoulos and Hall, J. Cell. Biol. (1989) 108:553-567.

Pitcher, J. A., J. Inglese, et al. (1992). "Role of beta gamma subunits of G proteins in targeting the beta-adrenergic receptor kinase to membrane-bound receptors." *Science* 257(5074): 1264-7.

Rothbard, J. B., S. Garlington, et al. (2000). "Conjugation of arginine oligomers to cyclosporin A facilitates topical delivery and inhibition of inflammation." *Nat Med* 6(11): 1253-7.

Ron, D., C. H. Chen, et al. (1994). "Cloning of an intracellular receptor for protein kinase C: a homolog of the beta subunit of G proteins." *Proc Natl Acad Sci U S A* 91(3): 839-43.

Ron, D., J. Luo, et al. (1995). "C2 region-derived peptides inhibit translocation and function of beta protein kinase C in vivo." *J Biol Chem* 270(41): 24180-7.

Ron, D. and D. Mochly-Rosen (1995). "An autoregulatory region in protein kinase C: the pseudoanchoring site." *Proc Natl Acad Sci U S A* 92(2): 492-6.

Saito et al., PNAS USA (1989) 86:3409-3413.

Schultz, J. E., A. K. Hsu, et al. (1996). "Morphine mimics the cardioprotective effect of ischemic preconditioning via a glibenclamide-sensitive mechanism in the rat heart." *Circ Res* 78(6): 1100-4.

Smith, B. L. and D. Mochly-Rosen (1992). "Inhibition of protein kinase C function by injection of intracellular receptors for the enzyme." *Biochem Biophys Res Commun* 188(3): 1235-40.

Speechly-Dick, M. E., M. M. Mocanu, et al. (1994). "Protein kinase C. Its role in ischemic preconditioning in the rat." *Circ Res* 75(3): 586-90.

Stebbins, E. G. and D. Mochly-Rosen (2001). "Binding specificity for RACK1 resides in the V5 region of beta II protein kinase C." *J Biol Chem* 276(32): 29644-50.

Theodore et al., J. Neurosci. (1995) 15:7158.

Vander Heide, R. S., D. Rim, et al. (1990). "An in vitro model of myocardial ischemia utilizing isolated adult rat myocytes." *J Mol Cell Cardiol* 22(2): 165-81.

Vives et al., J. Biol. Chem. (1997) 272:16010-16017.

Yenari, M. A., J. T. Palmer, et al. (1996). "Time-course and treatment response with SNX-111, an N-type calcium channel blocker, in a rodent model of focal cerebral ischemia using diffusion-weighted MRI." *Brain Res* 739(1-2): 36-45.

Fuchs, S., D. Bartfeld, et al. (1980). "Immune regulation of experimental myasthenia." *J Neurol Neurosurg Psychiatry* 43(7): 634-43.

Tarrab-Hazdai, R., Y. Schmidt-Sole, et al. (1980). "Modification of acetylcholine receptor: chemical and immunological characterization of polyalanyl acetylcholine receptor." *FEBS Lett* 118(1): 35-8.

Fuchs, S., D. Bartfeld, et al. (1981). "Molecular aspects of experimental autoimmune myasthenia gravis." *Prog Clin Biol Res* 63: 405-17.

Fuchs, S., D. Bartfeld, et al. (1981). "Acetylcholine receptor: molecular dissection and monoclonal antibodies in the study of experimental myasthenia." *Ann N Y Acad Sci* 377: 110-24.

Mochly-Rosen, D. and S. Fuchs (1981). "Monoclonal anti-acetylcholine-receptor antibodies directed against the cholinergic binding site." *Biochemistry* 20(20): 5920-4.

Goldberg, G., D. Mochly-Rosen, et al. (1983). "Monoclonal antibodies modify acetylcholine-induced ionic channel properties in cultured chick myoballs." *J Membr Biol* 76(2): 123-8.

Pizzighella, S., A. S. Gordon, et al. (1983). "An anti-acetylcholine receptor monoclonal antibody cross-reacts with phosvitin." *FEBS Lett* 159(1-2): 246-50.

Souroujon, M. C., D. Mochly-Rosen, et al. (1983). "Interaction of monoclonal antibodies to Torpedo acetylcholine receptor with the receptor of skeletal muscle." *Muscle Nerve* 6(4): 303-11.

Souroujon, M. C., S. Pizzighella, et al. (1985). "Antigenic specificity of acetylcholine receptor in developing muscle. Studies with monoclonal antibodies." *J Neuroimmunol* 8(2-3): 159-66.

Bollag, G. E., R. A. Roth, et al. (1986). "Protein kinase C directly phosphorylates the insulin receptor in vitro and reduces its protein-tyrosine kinase activity." *Proc Natl Acad Sci U S A* 83(16): 5822-4.

Baudier, J., D. Mochly-Rosen, et al. (1987). "Comparison of S100b protein with calmodulin: interactions with melittin and microtubule-associated tau proteins and inhibition of phosphorylation of tau proteins by protein kinase C." *Biochemistry* 26(10): 2886-93.

Krauss, S. W., D. Mochly-Rosen, et al. (1987). "Exposure of HeLa DNA polymerase alpha to protein kinase C affects its catalytic properties." *J Biol Chem* 262(8): 3432-5.

Mochly-Rosen, D., A. I. Basbaum, et al. (1987). "Distinct cellular and regional localization of immunoreactive protein kinase C in rat brain." *Proc Natl Acad Sci U S A* 84(13): 4660-4.

Mochly-Rosen, D. and D. E. Koshland, Jr. (1988). "A general procedure for screening inhibitory antibodies: application for identifying anti-protein kinase C antibodies." *Anal Biochem* 170(1): 31-7.

Mochly-Rosen, D., F. H. Chang, et al. (1988). "Chronic ethanol causes heterologous desensitization of receptors by reducing alpha s messenger RNA." *Nature* 333(6176): 848-50.

Gordon, A. S., L. Nagy, et al. (1990). "Chronic ethanol-induced heterologous desensitization is mediated by changes in adenosine transport." *Biochem Soc Symp* 56: 117-36.

Mochly-Rosen, D. and A. S. Gordon (1990). "GTP-binding proteins are restricted to signal transduction sites." *Biochem Biophys Res Commun* 173(1): 388-95.

Diamond, I., L. Nagy, et al. (1991). "The role of adenosine and adenosine transport in ethanol-induced cellular tolerance and dependence. Possible biologic and genetic markers of alcoholism." *Ann N Y Acad Sci* 625: 473-87.

Simon, A. J., Y. Milner, et al. (1991). "The identification and purification of a mammalian-like protein kinase C in the yeast Saccharomyces cerevisiae." *Proc Biol Sci* 243(1307): 165-71.

Mochly-Rosen, D., K. G. Miller, et al. (1992). "p65 fragments, homologous to the C2 region of protein kinase C, bind to the intracellular receptors for protein kinase C." *Biochemistry* 31(35): 8120-4.

Pitchford, S., J. W. Day, et al. (1992). "Nicotinic acetylcholine receptor desensitization is regulated by activation-induced extracellular adenosine accumulation." *J Neurosci* 12(11): 4540-4.

Simon, A. J., S. P. Saville, et al. (1993). "Characterization of PKC2, a gene encoding a second protein kinase C isotype of Saccharomyces cerevisiae." *Curr Biol* 3(12): 813-21.

Disatnik, M. H., A. R. Winnier, et al. (1994). "Distinct responses of protein kinase C isozymes to c-erbB-2 activation in SKBR-3 human breast carcinoma cells." *Cell Growth Differ* 5(8): 873-80.

Garcia-Navarro, S., Y. Marantz, et al. (1994). "Developmental expression of protein kinase C subspecies in rat brain-pituitary axis." *Mol Cell Endocrinol* 103(1-2): 133-8.

Brzoska, P. M., H. Chen, et al. (1995). "The product of the ataxia-telangiectasia group D complementing gene, ATDC, interacts with a protein kinase C substrate and inhibitor." *Proc Natl Acad Sci U S A* 92(17): 7824-8.

Disatnik, M. H., S. N. Jones, et al. (1995). "Stimulus-dependent subcellular localization of activated protein kinase C; a study with acidic fibroblast growth factor and transforming growth factor-beta 1 in cardiac myocytes." *J Mol Cell Cardiol* 27(11): 2473-81.

Johnson, J. A., S. Adak, et al. (1995). "Prolonged phorbol ester treatment down-regulates protein kinase C isozymes and increases contraction rate in neonatal cardiac myocytes." *Life Sci* 57(11): 1027-38.

Smith, B. L., B. W. Krushelnycky, et al. (1996). "The HIV nef protein associates with protein kinase C theta." *J Biol Chem* 271(28): 16753-7.

Zhou, L. Y., M. Disatnik, et al. (1996). "Differential activation of protein kinase C isozymes by phorbol ester and collagen in human skin microvascular endothelial cells." *J Invest Dermatol* 107(2): 248-52.

Hundle, B., T. McMahon, et al. (1997). "An inhibitory fragment derived from protein kinase Cepsilon prevents enhancement of nerve growth factor responses by ethanol and phorbol esters." *J Biol Chem* 272(23): 15028-35.

Yedovitzky, M., D. Mochly-Rosen, et al. (1997). "Translocation inhibitors define specificity of protein kinase C isoenzymes in pancreatic beta-cells." *J Biol Chem* 272(3): 1417-20.

Zhang, Z. H., J. A. Johnson, et al. (1997). "C2 region-derived peptides of beta-protein kinase C regulate cardiac Ca2+ channels." *Circ Res* 80(5): 720-9.

Csukai, M. and D. Mochly-Rosen (1998). "Molecular genetic approaches. II. Expression-interaction cloning." *Methods Mol Biol* 88: 133-9.

Laudanna, C., D. Mochly-Rosen, et al. (1998). "Evidence of zeta protein kinase C involvement in polymorphonuclear neutrophil integrin-dependent adhesion and chemotaxis." *J Biol Chem* 273(46): 30306-15.

Mochly-Rosen, D. and L. M. Kauvar (1998). "Modulating protein kinase C signal transduction." *Adv Pharmacol* 44: 91-145.

Knauf, J. A., R. Elisei, et al. (1999). "Involvement of protein kinase Cepsilon (PKCepsilon) in thyroid cell death. A truncated chimeric PKCepsilon cloned from a thyroid cancer cell line protects thyroid cells from apoptosis." *J Biol Chem* 274(33): 23414-25.

Rodriguez, M. M., D. Ron, et al. (1999). "RACK1, a protein kinase C anchoring protein, coordinates the binding of activated protein kinase C and select pleckstrin homology domains in vitro." *Biochemistry* 38(42): 13787-94.

Rodriguez, M. M., C. H. Chen, et al. (1999). "Characterization of the binding and phosphorylation of cardiac calsequestrin by epsilon protein kinase C." *FEBS Lett* 454(3): 240-6.

Aley, K. O., R. O. Messing, et al. (2000). "Chronic hypersensitivity for inflammatory nociceptor sensitization mediated by the epsilon isozyme of protein kinase C." *J Neurosci* 20(12): 4680-5.

Dempsey, E. C., A. C. Newton, et al. (2000). "Protein kinase C isozymes and the regulation of diverse cell responses." *Am J Physiol Lung Cell Mol Physiol* 279(3): L429-38.

Hu, K., D. Mochly-Rosen, et al. (2000). "Evidence for functional role of epsilonPKC isozyme in the regulation of cardiac Ca(2+) channels." *Am J Physiol Heart Circ Physiol* 279(6): H2658-64.

Mackay, K. and D. Mochly-Rosen (2000). "Involvement of a p38 mitogen-activated protein kinase phosphatase in protecting neonatal rat cardiac myocytes from ischemia." *J Mol Cell Cardiol* 32(8): 1585-8.

Mochly-Rosen, D. and L. M. Kauvar (2000). "Pharmacological regulation of network kinetics by protein kinase C localization." *Semin Immunol* 12(1): 55-61.

Mochly-Rosen, D., J. A. Fagin, et al. (2001). "Spontaneous occurrence of an inhibitor of protein kinase C localization in a thyroid cancer cell line: role in thyroid tumorigenesis." *Adv Enzyme Regul* 41: 87-97.

Inagaki et al., Circulation (2003) 108(7):869-875.

Inagaki et al., Circulation (2003) 108(19):2304-2307.

Nishikawa et al., Journal of Biological Chemistry (1997)272(2):952-960.

Souroujon et al., Nature Biotechnology (1998) 16(10):919.

Supplementary European Search Report for EP 01 99 5483, mailed on Dec. 21, 2004, 7 pages.

Chen et al., Circulation (2000) 102(18 Suppl. II):120.

Chen et al., PNAS USA (1999) 96(22):12784-12789.

Chen et al., PNAS USA (2001) 98(20):11114-11119.

Csukai et al., Pharmacological Research (1999) 39(4):253-259.

Inagaki et al., Circulation (2000) 101(7):797-804.

Inagaki et al., Circulation (2003) 108(7):869-875.

Inagaki et al., Circulation (2003) 108(19):2304-2307.

Johnson et al., Journal of Biological Chemistry (1996) 271(40):24962-24966.

Miettinen et al., J. Neurosci. (1996) 16(19):6236-6245.

Miyawaki et al., Circulation Res. (1997) 80(6):790.

Mochly-Rosen, Science (1995) 268:247-251.

Mochly-Rosen, PNAS USA (1991) 88:3997-4000.

Nishikawa et al., Journal of Biological Chemistry (1997) 272(2):952-960.

Shizukuda et al., Circulation (1999) 100(18):1909-1916.

Souroujon et al., Nature Biotechnology (1998) 16(10):919.

Supplementary European Search Report for EP 01 99 5483, mailed on Dec. 21, 2004, 7 pages.

Way et al., Trends in Pharmacological Sciences (2000) 21(5):181-187.

Yoshida et al., Biochimica et Biophysica Acta (1999) 14:230-238.

Gayle et al., J Biol Chem (1993) 268(29):22105-22111.

Whisstock and Lesk, Qtrly Rev Biophys (2003) 36(3):307-340.

USPTO in house Blast search with $NP_{13}$ 057853, performed Dec. 10, 2009.

* cited by examiner

```
              δV1-1                              δV1-2
           ┌─────────┐                        ┌─────────┐
δPKC  MAPFLRISF NSYELGSLQA  EDDASQPFCA VKMKEALTTD RGKTLVQKKP TMYPEW
θPKC  MSPFLRIGL SNFDCGSCQS  CQGEAVNPYCA VLVKEYVESE NGQMYIQKKP TMYPPW
                ψεR
           ┌─────────┐
KSTF DAHIYEGRVI QIVLMRAAED PMSEVTVGVS VLAERCKKNN GKAEFWLDL QPQAKVLMCV QYFLE
DSTF DAHINKGRVM QIIVKGKNVD LISETTVELY SLAERCRKNN GKTEIWLEL KPQGRMLMNA RYFLE
```

Fig. 1

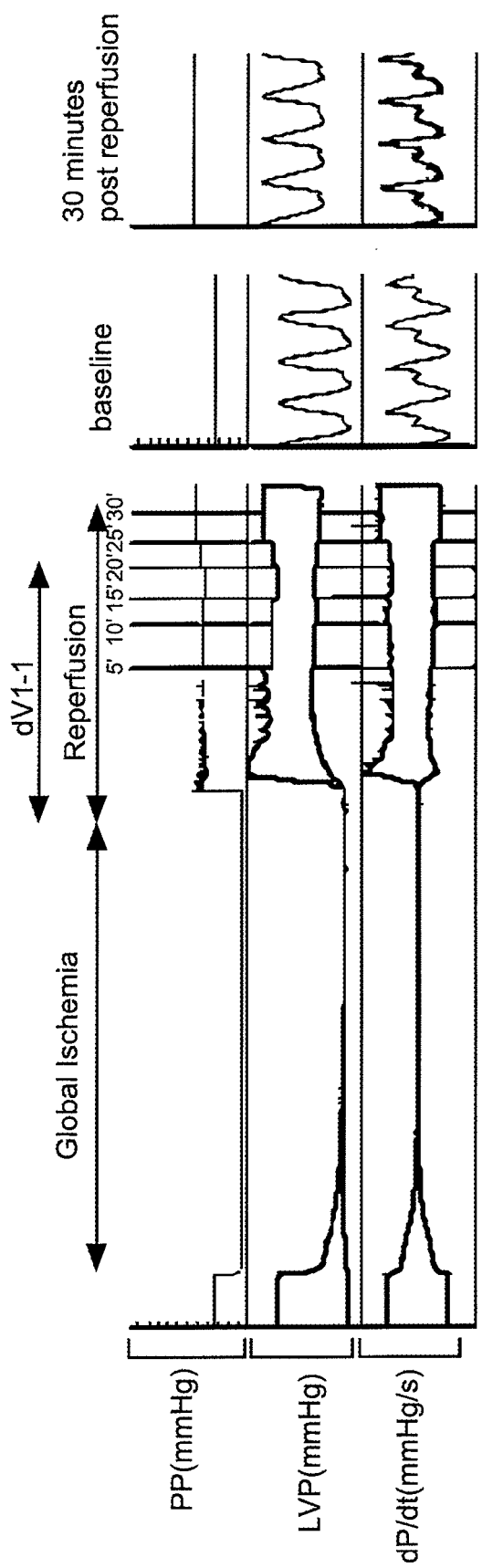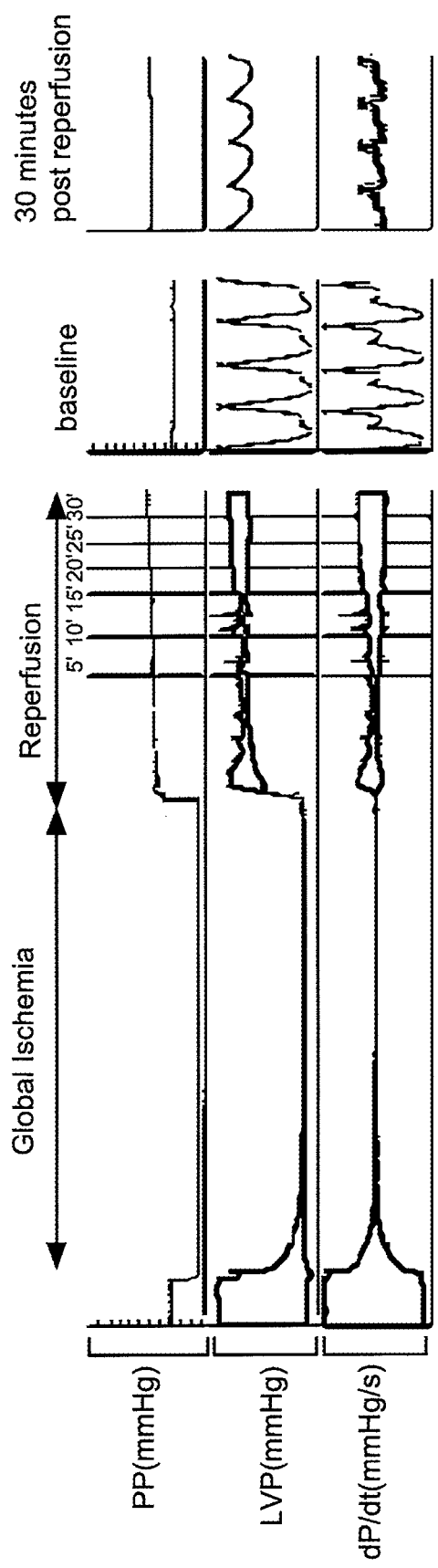

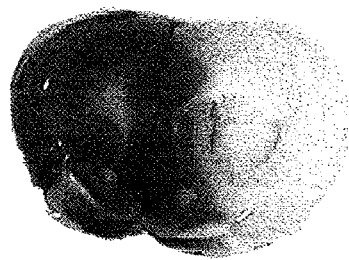
Fig. 11A
Fig. 11B

SEQUENCE LISTING

```
<160> NUMBER OF SEQ ID NOS: 72

<210> SEQ ID NO 1
<211> LENGTH: 8
<212> TYPE: PRT
<213> ORGANISM: Artificial Sequence
<220> FEATURE:
<223> OTHER INFORMATION: epsilon V1-2, residues 14-21 of epsilon-PKC

<400> SEQUENCE: 1

Glu Ala Val Ser Leu Lys Pro Thr
1               5

<210> SEQ ID NO 2
<211> LENGTH: 141
<212> TYPE: PRT
<213> ORGANISM: Rattus norvegicus

<400> SEQUENCE: 2

Met Ala Pro Phe Leu Arg Ile Ser Phe Asn Ser Tyr Glu Leu Gly Ser
1               5                   10                  15

Leu Gln Ala Glu Asp Asp Ala Ser Gln Pro Phe Cys Ala Val Lys Met
            20                  25                  30

Lys Glu Ala Leu Thr Thr Asp Arg Gly Lys Thr Leu Val Gln Lys Lys
        35                  40                  45
```

-continued

Pro Thr Met Tyr Pro Glu Trp Lys Ser Thr Phe Asp Ala His Ile Tyr
           50                  55                  60

Glu Gly Arg Val Ile Gln Ile Val Leu Met Arg Ala Ala Glu Asp Pro
65                  70                  75                  80

Met Ser Glu Val Thr Val Gly Val Ser Val Leu Ala Gly Arg Cys Lys
                85                  90                  95

Lys Asn Asn Gly Lys Ala Glu Phe Trp Leu Asp Leu Gln Pro Gln Ala
            100                 105                 110

Lys Val Leu Met Cys Val Gln Tyr Phe Leu Glu Asp Gly Asp Cys Lys
        115                 120                 125

Gln Ser Met Arg Ser Glu Glu Ala Met Phe Pro Thr
    130                 135                 140

<210> SEQ ID NO 3
<211> LENGTH: 124
<212> TYPE: PRT
<213> ORGANISM: Mus musculus

<400> SEQUENCE: 3

Met Ser Pro Phe Leu Arg Ile Gly Leu Ser Asn Phe Asp Cys Gly Ser
1               5                   10                  15

Cys Gln Ser Cys Gln Gly Glu Ala Val Asn Pro Tyr Cys Ala Val Leu
            20                  25                  30

Val Lys Glu Tyr Val Glu Ser Glu Asn Gly Gln Met Tyr Ile Gln Lys
        35                  40                  45

Lys Pro Thr Met Tyr Pro Pro Trp Asp Ser Thr Phe Asp Ala His Ile
    50                  55                  60

Asn Lys Gly Arg Val Met Gln Ile Ile Val Lys Gly Lys Asn Val Asp
65                  70                  75                  80

Leu Ile Ser Glu Thr Thr Val Glu Leu Tyr Ser Leu Ala Glu Arg Cys
                85                  90                  95

Arg Lys Asn Asn Gly Lys Thr Glu Ile Trp Leu Glu Leu Lys Pro Gln
            100                 105                 110

Gly Arg Met Leu Met Asn Ala Arg Tyr Phe Leu Glu
        115                 120

<210> SEQ ID NO 4
<211> LENGTH: 10
<212> TYPE: PRT
<213> ORGANISM: Rattus norvegicus

<400> SEQUENCE: 4

Ser Phe Asn Ser Tyr Glu Leu Gly Ser Leu
1               5                   10

<210> SEQ ID NO 5
<211> LENGTH: 10
<212> TYPE: PRT
<213> ORGANISM: Rattus norvegicus

<400> SEQUENCE: 5

Ala Leu Thr Thr Asp Arg Gly Lys Leu Val
1               5                   10

<210> SEQ ID NO 6
<211> LENGTH: 8
<212> TYPE: PRT
<213> ORGANISM: Rattus norvegicus

```
<400> SEQUENCE: 6

Met Arg Ala Ala Glu Asp Pro Met
1               5

<210> SEQ ID NO 7
<211> LENGTH: 58
<212> TYPE: PRT
<213> ORGANISM: Rattus norvegicus

<400> SEQUENCE: 7

Pro Phe Arg Pro Lys Val Lys Ser Pro Arg Asp Tyr Ser Asn Phe Asp
1               5                   10                  15

Gln Glu Phe Leu Asn Glu Lys Ala Arg Leu Ser Tyr Ser Asp Lys Asn
            20                  25                  30

Leu Ile Asp Ser Met Asp Gln Ser Ala Phe Ala Gly Phe Ser Phe Val
        35                  40                  45

Asn Pro Lys Phe Glu His Leu Leu Glu Asp
    50                  55

<210> SEQ ID NO 8
<211> LENGTH: 17
<212> TYPE: PRT
<213> ORGANISM: Artificial Sequence
<220> FEATURE:
<223> OTHER INFORMATION: Drosophila Antennapedia homeodomain-derived
      carrier peptide

<400> SEQUENCE: 8

Cys Arg Gln Ile Lys Ile Trp Phe Gln Asn Arg Arg Met Lys Trp Lys
1               5                   10                  15

Lys

<210> SEQ ID NO 9
<211> LENGTH: 11
<212> TYPE: PRT
<213> ORGANISM: Artificial Sequence
<220> FEATURE:
<223> OTHER INFORMATION: Tat-derived carrier peptide

<400> SEQUENCE: 9

Tyr Gly Arg Lys Lys Arg Arg Gln Arg Arg Arg
1               5                   10

<210> SEQ ID NO 10
<211> LENGTH: 6
<212> TYPE: PRT
<213> ORGANISM: Artificial Sequence
<220> FEATURE:
<223> OTHER INFORMATION: beta-PKC-selective activator peptide

<400> SEQUENCE: 10

Ser Val Glu Ile Trp Asp
1               5

<210> SEQ ID NO 11
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 11

Met Lys Ala Ala Glu Asp Pro Met
1               5
```

```
<210> SEQ ID NO 12
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 12

Met Arg Gly Ala Glu Asp Pro Met
 1               5

<210> SEQ ID NO 13
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 13

Met Arg Ala Gly Glu Asp Pro Met
 1               5

<210> SEQ ID NO 14
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 14

Met Arg Ala Pro Glu Asp Pro Met
 1               5

<210> SEQ ID NO 15
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 15

Met Arg Ala Asn Glu Asp Pro Met
 1               5

<210> SEQ ID NO 16
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 16

Met Arg Ala Ala Asp Asp Pro Met
 1               5

<210> SEQ ID NO 17
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 17

Met Arg Ala Ala Glu Asp Pro Val
 1               5
```

```
<210> SEQ ID NO 18
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 18

Met Arg Ala Ala Glu Asp Pro Ile
 1               5

<210> SEQ ID NO 19
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 19

Met Arg Ala Ala Glu Asp Pro Leu
 1               5

<210> SEQ ID NO 20
<211> LENGTH: 4
<212> TYPE: PRT
<213> ORGANISM: Rattus norvegicus

<400> SEQUENCE: 20

Glu Asp Pro Met
 1

<210> SEQ ID NO 21
<211> LENGTH: 5
<212> TYPE: PRT
<213> ORGANISM: Rattus norvegicus

<400> SEQUENCE: 21

Ala Glu Asp Pro Met
 1               5

<210> SEQ ID NO 22
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 22

Met Arg Ala Ala Glu Asp Met Pro
 1               5

<210> SEQ ID NO 23
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 23

Met Glu Ala Ala Glu Asp Pro Met
 1               5

<210> SEQ ID NO 24
<211> LENGTH: 8
<212> TYPE: PRT
<213> ORGANISM: Artificial Sequence
<220> FEATURE:
<223> OTHER INFORMATION: modified pseudo-delta RACK peptide
```

<400> SEQUENCE: 24

Met Asp Ala Ala Glu Asp Pro Met
1               5

<210> SEQ ID NO 25
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 25

Met Arg Ala Ala Glu Glu Pro Leu
1               5

<210> SEQ ID NO 26
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 26

Met Arg Ala Ala Glu Asp Pro Leu
1               5

<210> SEQ ID NO 27
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 27

Met Arg Ala Ala Glu Glu Pro Ile
1               5

<210> SEQ ID NO 28
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 28

Met Arg Ala Ala Glu Glu Pro Val
1               5

<210> SEQ ID NO 29
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 29

Met Arg Ala Ala Glu Asp Pro Val
1               5

<210> SEQ ID NO 30
<211> LENGTH: 8
<212> TYPE: PRT
<213> ORGANISM: Artificial Sequence
<220> FEATURE:
<223> OTHER INFORMATION: modified pseudo-delta RACK peptide

```
<400> SEQUENCE: 30

Met Arg Ala Ala Asn Asp Pro Met
1               5

<210> SEQ ID NO 31
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 31

Met Arg Ala Ala Gln Asp Pro Met
1               5

<210> SEQ ID NO 32
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 32

Met Arg Ala Ala Glu Gln Pro Met
1               5

<210> SEQ ID NO 33
<211> LENGTH: 8
<212> TYPE: PRT
<213> ORGANISM: Artificial Sequence
<220> FEATURE:
<223> OTHER INFORMATION: modified pseudo-delta RACK peptide

<400> SEQUENCE: 33

Met Arg Ala Ala Glu Asn Pro Met
1               5

<210> SEQ ID NO 34
<211> LENGTH: 10
<212> TYPE: PRT
<213> ORGANISM: Artificial Sequence
<220> FEATURE:
<223> OTHER INFORMATION: modified delta V1-1 peptide

<400> SEQUENCE: 34

Thr Phe Asn Ser Tyr Glu Leu Gly Ser Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: modified delta V1-1 peptide

<400> SEQUENCE: 35

Ala Phe Asn Ser Tyr Glu Leu Gly Ser Leu
1               5                   10

<210> SEQ ID NO 36
<211> LENGTH: 10
<212> TYPE: PRT
<213> ORGANISM: Artificial Sequence
<220> FEATURE:
<223> OTHER INFORMATION: modified delta V1-1 peptide
```

```
<400> SEQUENCE: 36

Ser Phe Asn Ser Tyr Glu Leu Gly Thr Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: modified delta V1-1 peptide

<400> SEQUENCE: 37

Thr Phe Asn Ser Tyr Glu Leu Gly Thr Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: modified delta V1-1 peptide

<400> SEQUENCE: 38

Ser Tyr Asn Ser Tyr Glu Leu Gly Ser Leu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: modified delta V1-1 peptide

<400> SEQUENCE: 39

Ser Phe Asn Ser Phe Glu Leu Gly Ser Leu
1               5                   10

<210> SEQ ID NO 40
<211> LENGTH: 9
<212> TYPE: PRT
<213> ORGANISM: Artificial Sequence
<220> FEATURE:
<223> OTHER INFORMATION: modified delta V1-1 peptide

<400> SEQUENCE: 40

Ser Asn Ser Tyr Asp Leu Gly Ser Leu
1               5

<210> SEQ ID NO 41
<211> LENGTH: 10
<212> TYPE: PRT
<213> ORGANISM: Artificial Sequence
<220> FEATURE:
<223> OTHER INFORMATION: modified delta V1-1 peptide

<400> SEQUENCE: 41

Ser Phe Asn Ser Tyr Glu Leu Pro Ser Leu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: modified delta V1-1 peptide
```

```
<400> SEQUENCE: 42

Ser Phe Asn Ser Tyr Glu Ile Gly Ser Val
1               5                   10

<210> SEQ ID NO 43
<211> LENGTH: 10
<212> TYPE: PRT
<213> ORGANISM: Artificial Sequence
<220> FEATURE:
<223> OTHER INFORMATION: modified delta V1-1 peptide

<400> SEQUENCE: 43

Ser Phe Asn Ser Tyr Glu Val Gly Ser Ile
1               5                   10

<210> SEQ ID NO 44
<211> LENGTH: 10
<212> TYPE: PRT
<213> ORGANISM: Artificial Sequence
<220> FEATURE:
<223> OTHER INFORMATION: modified delta V1-1 peptide

<400> SEQUENCE: 44

Ser Phe Asn Ser Tyr Glu Leu Gly Ser Val
1               5                   10

<210> SEQ ID NO 45
<211> LENGTH: 10
<212> TYPE: PRT
<213> ORGANISM: Artificial Sequence
<220> FEATURE:
<223> OTHER INFORMATION: modified delta V1-1 peptide

<400> SEQUENCE: 45

Ser Phe Asn Ser Tyr Glu Leu Gly Ser Ile
1               5                   10

<210> SEQ ID NO 46
<211> LENGTH: 10
<212> TYPE: PRT
<213> ORGANISM: Artificial Sequence
<220> FEATURE:
<223> OTHER INFORMATION: modified delta V1-1 peptide

<400> SEQUENCE: 46

Ser Phe Asn Ser Tyr Glu Ile Gly Ser Leu
1               5                   10

<210> SEQ ID NO 47
<211> LENGTH: 10
<212> TYPE: PRT
<213> ORGANISM: Artificial Sequence
<220> FEATURE:
<223> OTHER INFORMATION: modified delta V1-1 peptide

<400> SEQUENCE: 47

Ser Phe Asn Ser Tyr Glu Val Gly Ser Leu
1               5                   10

<210> SEQ ID NO 48
<211> LENGTH: 10
<212> TYPE: PRT
<213> ORGANISM: Artificial Sequence
<220> FEATURE:
<223> OTHER INFORMATION: modified delta V1-1 peptide
```

```
<400> SEQUENCE: 48

Ala Phe Asn Ser Tyr Glu Leu Gly Ser Leu
1               5                   10

<210> SEQ ID NO 49
<211> LENGTH: 6
<212> TYPE: PRT
<213> ORGANISM: Rattus norvegicus

<400> SEQUENCE: 49

Tyr Glu Leu Gly Ser Leu
1               5

<210> SEQ ID NO 50
<211> LENGTH: 6
<212> TYPE: PRT
<213> ORGANISM: Artificial Sequence
<220> FEATURE:
<223> OTHER INFORMATION: modified fragment of delta V1-1 peptide

<400> SEQUENCE: 50

Tyr Asp Leu Gly Ser Leu
1               5

<210> SEQ ID NO 51
<211> LENGTH: 6
<212> TYPE: PRT
<213> ORGANISM: Artificial Sequence
<220> FEATURE:
<223> OTHER INFORMATION: modified fragment of delta V1-1 peptide

<400> SEQUENCE: 51

Phe Asp Leu Gly Ser Leu
1               5

<210> SEQ ID NO 52
<211> LENGTH: 6
<212> TYPE: PRT
<213> ORGANISM: Artificial Sequence
<220> FEATURE:
<223> OTHER INFORMATION: modified fragment of delta V1-1 peptide

<400> SEQUENCE: 52

Tyr Asp Ile Gly Ser Leu
1               5

<210> SEQ ID NO 53
<211> LENGTH: 6
<212> TYPE: PRT
<213> ORGANISM: Artificial Sequence
<220> FEATURE:
<223> OTHER INFORMATION: modified fragment of delta V1-1 peptide

<400> SEQUENCE: 53

Tyr Asp Val Gly Ser Leu
1               5

<210> SEQ ID NO 54
<211> LENGTH: 6
<212> TYPE: PRT
<213> ORGANISM: Artificial Sequence
<220> FEATURE:
<223> OTHER INFORMATION: modified fragment of delta V1-1 peptide

<400> SEQUENCE: 54

Tyr Asp Leu Pro Ser Leu
1               5
```

```
<210> SEQ ID NO 55
<211> LENGTH: 6
<212> TYPE: PRT
<213> ORGANISM: Artificial Sequence
<220> FEATURE:
<223> OTHER INFORMATION: modified fragment of delta V1-1 peptide

<400> SEQUENCE: 55

Tyr Asp Leu Gly Leu Leu
 1               5

<210> SEQ ID NO 56
<211> LENGTH: 6
<212> TYPE: PRT
<213> ORGANISM: Artificial Sequence
<220> FEATURE:
<223> OTHER INFORMATION: modified fragment of delta V1-1 peptide

<400> SEQUENCE: 56

Tyr Asp Leu Gly Ser Ile
 1               5

<210> SEQ ID NO 57
<211> LENGTH: 6
<212> TYPE: PRT
<213> ORGANISM: Artificial Sequence
<220> FEATURE:
<223> OTHER INFORMATION: modified fragment of delta V1-1 peptide

<400> SEQUENCE: 57

Tyr Asp Leu Gly Ser Val
 1               5

<210> SEQ ID NO 58
<211> LENGTH: 4
<212> TYPE: PRT
<213> ORGANISM: Rattus norvegicus

<400> SEQUENCE: 58

Leu Gly Ser Leu
 1

<210> SEQ ID NO 59
<211> LENGTH: 4
<212> TYPE: PRT
<213> ORGANISM: Artificial Sequence
<220> FEATURE:
<223> OTHER INFORMATION: modified fragment of delta V1-1 peptide

<400> SEQUENCE: 59

Ile Gly Ser Leu
 1

<210> SEQ ID NO 60
<211> LENGTH: 4
<212> TYPE: PRT
<213> ORGANISM: Artificial Sequence
<220> FEATURE:
<223> OTHER INFORMATION: modified fragment of delta V1-1 peptide

<400> SEQUENCE: 60

Val Gly Ser Leu
 1

<210> SEQ ID NO 61
<211> LENGTH: 4
<212> TYPE: PRT
<213> ORGANISM: Artificial Sequence
```

```
<220> FEATURE:
<223> OTHER INFORMATION: modified fragment of delta V1-1 peptide

<400> SEQUENCE: 61

Leu Pro Ser Leu
 1

<210> SEQ ID NO 62
<211> LENGTH: 4
<212> TYPE: PRT
<213> ORGANISM: Artificial Sequence
<220> FEATURE:
<223> OTHER INFORMATION: modified fragment of delta V1-1 peptide

<400> SEQUENCE: 62

Leu Gly Leu Leu
 1

<210> SEQ ID NO 63
<211> LENGTH: 4
<212> TYPE: PRT
<213> ORGANISM: Artificial Sequence
<220> FEATURE:
<223> OTHER INFORMATION: modified fragment of delta V1-1 peptide

<400> SEQUENCE: 63

Leu Gly Ser Ile
 1

<210> SEQ ID NO 64
<211> LENGTH: 4
<212> TYPE: PRT
<213> ORGANISM: Artificial Sequence
<220> FEATURE:
<223> OTHER INFORMATION: modified fragment of delta V1-1 peptide

<400> SEQUENCE: 64

Leu Gly Ser Val
 1

<210> SEQ ID NO 65
<211> LENGTH: 11
<212> TYPE: PRT
<213> ORGANISM: Artificial Sequence
<220> FEATURE:
<223> OTHER INFORMATION: modified delta V1-2 peptide

<400> SEQUENCE: 65

Ala Leu Ser Thr Asp Arg Gly Lys Thr Leu Val
 1               5                  10

<210> SEQ ID NO 66
<211> LENGTH: 11
<212> TYPE: PRT
<213> ORGANISM: Artificial Sequence
<220> FEATURE:
<223> OTHER INFORMATION: modified delta V1-2 peptide

<400> SEQUENCE: 66

Ala Leu Thr Ser Asp Arg Gly Lys Thr Leu Val
 1               5                  10

<210> SEQ ID NO 67
<211> LENGTH: 11
<212> TYPE: PRT
<213> ORGANISM: Artificial Sequence
<220> FEATURE:
<223> OTHER INFORMATION: modified delta V1-2 peptide
```

```
<400> SEQUENCE: 67

Ala Leu Thr Thr Asp Arg Gly Lys Ser Leu Val
1               5                   10

<210> SEQ ID NO 68
<211> LENGTH: 11
<212> TYPE: PRT
<213> ORGANISM: Artificial Sequence
<220> FEATURE:
<223> OTHER INFORMATION: modified delta V1-2 peptide

<400> SEQUENCE: 68

Ala Leu Thr Thr Asp Arg Pro Lys Thr Leu Val
1               5                   10

<210> SEQ ID NO 69
<211> LENGTH: 11
<212> TYPE: PRT
<213> ORGANISM: Artificial Sequence
<220> FEATURE:
<223> OTHER INFORMATION: modified delta V1-2 peptide

<400> SEQUENCE: 69

Ala Leu Thr Thr Asp Arg Gly Arg Thr Leu Val
1               5                   10

<210> SEQ ID NO 70
<211> LENGTH: 11
<212> TYPE: PRT
<213> ORGANISM: Artificial Sequence
<220> FEATURE:
<223> OTHER INFORMATION: modified delta V1-2 peptide

<400> SEQUENCE: 70

Ala Leu Thr Thr Asp Lys Gly Lys Thr Leu Val
1               5                   10

<210> SEQ ID NO 71
<211> LENGTH: 11
<212> TYPE: PRT
<213> ORGANISM: Artificial Sequence
<220> FEATURE:
<223> OTHER INFORMATION: modified delta V1-2 peptide

<400> SEQUENCE: 71

Ala Leu Thr Thr Asp Lys Gly Lys Thr Leu Val
1               5                   10

<210> SEQ ID NO 72
<211> LENGTH: 320
<212> TYPE: PRT
<213> ORGANISM: Homo sapiens

<400> SEQUENCE: 72

Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
                20                  25                  30

Thr Asp Glu Glu Ser Ile Leu Thr Leu Leu Thr Ser Arg Ser Asn Ala
            35                  40                  45

Gln Arg Gln Glu Ile Ser Ala Ala Phe Lys Thr Leu Phe Gly Arg Asp
        50                  55                  60

Leu Leu Asp Asp Leu Lys Ser Glu Leu Thr Gly Lys Phe Glu Lys Leu
65                  70                  75                  80
```

-continued

```
Ile Val Ala Leu Met Lys Pro Ser Arg Leu Tyr Asp Ala Tyr Glu Leu
             85                  90                  95
Lys His Ala Leu Lys Gly Ala Gly Thr Asn Glu Lys Val Leu Thr Glu
            100                 105                 110
Ile Ile Ala Ser Arg Thr Pro Glu Glu Leu Arg Ala Ile Lys Gln Val
            115                 120                 125
Tyr Glu Glu Glu Tyr Gly Ser Ser Leu Glu Asp Asp Val Val Gly Asp
    130                 135                 140
Thr Ser Gly Tyr Tyr Gln Arg Met Leu Val Val Leu Leu Gln Ala Asn
145                 150                 155                 160
Arg Asp Pro Asp Ala Gly Ile Asp Glu Ala Gln Val Glu Gln Asp Ala
                165                 170                 175
Gln Ala Leu Phe Gln Ala Gly Glu Leu Lys Trp Gly Thr Asp Glu Glu
            180                 185                 190
Lys Phe Ile Thr Ile Phe Gly Thr Arg Ser Val Ser His Leu Arg Lys
            195                 200                 205
Val Phe Asp Lys Tyr Met Thr Ile Ser Gly Phe Gln Ile Glu Glu Thr
    210                 215                 220
Ile Asp Arg Glu Thr Ser Gly Asn Leu Glu Gln Leu Leu Leu Ala Val
225                 230                 235                 240
Val Lys Ser Ile Arg Ser Ile Pro Ala Tyr Leu Ala Glu Thr Leu Tyr
                245                 250                 255
Tyr Ala Met Lys Gly Ala Gly Thr Asp Asp His Thr Leu Ile Arg Val
            260                 265                 270
Met Val Ser Arg Ser Glu Ile Asp Leu Phe Asn Ile Arg Lys Glu Phe
            275                 280                 285
Arg Lys Asn Phe Ala Thr Ser Leu Tyr Ser Met Ile Lys Gly Asp Thr
    290                 295                 300
Ser Gly Asp Tyr Lys Lys Ala Leu Leu Leu Leu Cys Gly Glu Asp Asp
305                 310                 315                 320
```

METHOD FOR REDUCING CENTRAL NERVOUS SYSTEM TISSUE OR CELL DAMAGE IN A SUBJECT DUE TO STROKE

CROSS-REFERENCE TO RELATED APPLICATIONS

This application is a continuation of U.S. application Ser. No. 10/843,731, filed on May 12, 2004, which is now U.S. Pat. No. 7,745,388, and which is a divisional of U.S. application Ser. No. 10/007,761, filed on Nov. 9, 2001, which is now U.S. Pat. No. 6,855,693, which claims the benefit of priority of U.S. Provisional Application No. 60/262,060, filed on Jan. 18, 2001, now expired; all of these applications are hereby incorporated by reference in their entirety.

STATEMENT OF RIGHTS TO INVENTIONS MADE UNDER FEDERALLY SPONSORED RESEARCH

This work was supported in part by the National Institutes of Health Grant HL 52141. The United States government may have certain rights in this invention.

REFERENCE TO SEQUENCE LISTING SUBMITTED VIA EFS-WEB

The entire content of the following electronic submission of the sequence listing via the USPTO EFS-WEB server, as authorized and set forth in the Manual of Patent Examining Procedure (MPEP) §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 578422000402Seqlist.txt | Oct. 6, 2009 | 17,607 bytes |

FIELD OF THE INVENTION

The present invention relates to peptides effective to activate or inhibit translocation and/or function of δPKC. The present invention also relates to therapeutic compositions and methods for treating diseases or conditions which are benefited by inhibition or activation of δPKC.

BACKGROUND OF THE INVENTION

Protein kinase C (PKC) is a key enzyme in signal transduction involved in a variety of cellular functions, including cell growth, regulation of gene expression and ion channel activity. The PKC family of isozymes includes at least 11 different protein kinases which can be divided into at least three subfamilies based on their homology and sensitivity to activators. Members of the classical or cPKC subfamily, $\alpha$, $\beta_I$, $\beta_{II}$, and $\gamma$PKC, contain four homologous domains (C1, C2, C3 and C4) inter-spaced with isozyme-unique (variable or V) regions, and require calcium, phosphatidylserine (PS), and diacylglycerol (DG) or phorbol esters for activation. Members of the novel or nPKC subfamily, δ, ε, η, and θPKC, lack the C2 homologous domain and do not require calcium for activation. Finally, members of the atypical or a PKC subfamily, ζ and λ/ι PKC, lack both the C2 and one half of the C1 homologous domains and are insensitive to DG, phorbol esters and calcium.

Studies on the subcellular distribution of PKC isozymes demonstrate that activation of PKC results in its redistribution in the cells (also termed translocation).

It appears that the unique cellular functions of different PKC isozymes are determined by their subcellular location. For example, activated $\beta_I$PKC is found inside the nucleus, whereas activated $\beta_{II}$PKC is found at the perinucleus and cell periphery of cardiac myocytes (Disatnik, M. H., et al., *Exp. Cell Res.* 210:287-297 (1994)). Further, in the same cells, εPKC binds to cross-striated structures (possibly the contractile elements) and cell-cell contacts following activation or after addition of exogenous activated εPKC to fixed cells (Mochly-Rosen, et al., 1990; Disatnik, et al., 1994). The localization of different PKC isozymes to different areas of the cell in turn appears due to binding of the activated isozymes to specific anchoring molecules termed Receptors for Activated C-Kinase (RACKs).

RACKs are thought to function by selectively anchoring activated PKC isozymes to their respective subcellular sites. RACKs bind only fully activated PKC and are not necessarily substrates of the enzyme. Nor is the binding to RACKs mediated via the catalytic domain of the kinase (Mochly-Rosen, D., et al., *Proc. Natl. Acad. Sci. USA* 88:3997-4000 (1991)). Translocation of PKC reflects binding of the activated enzyme to RACKs anchored to the cell particulate fraction and the binding to RACKs is required for PKC to produce its cellular responses (Mochly-Rosen, D., et al., *Science* 268:247-251 (1995)). Inhibition of PKC binding to RACKs in vivo inhibits PKC translocation and PKC-mediated function (Johnson, J. A., et al., *J. Biol. Chem* 271:24962-24966 (1996a); Ron, D., et al., *Proc. Natl. Acad. Sci. USA* 92:492-496 (1995); Smith, B. L. and Mochly-Rosen, D., *Biochem. Biophys. Res. Commun.* 188:1235-1240 (1992)).

cDNA clones encoding RACK1 and RACK2 have been identified (U.S. Pat. No. 5,519,003; Ron, D., et al., *Proc. Natl. Acad. Sci. USA* 91:839-843 (1994); Csukai, M., et al., $9^{TH}$ INTERNATIONAL CONFERENCE ON SECOND MESSENGERS AND PHOSPHOPROTEINS 112 (1995)). Both are homologs of the β subunit of G proteins, a receptor for another translocating protein kinase, the β-adrenergic receptor kinase, βARK (Pitcher, J., et al., *Science* 257:1264-1267 (1992)). Similar to Gβ, RACK1, and RACK2 have seven WD40 repeats (Ron, et al., 1994; Csukai, et al., 1995). Recent data suggest that RACK1 is a $\beta_{II}$PKC-specific RACK (Stebbins, E. G., et al., *J. Biol. Chem.* 276:29644-29650 (2001)) and that RACK2 (Csukai, M., et al, *J. Biol. Chem.* 272:29200-29206 (1997)) is specific for activated εPKC.

Translocation of PKC is required for proper function of PKC isozymes. Peptides that mimic either the PKC-binding site on RACKs (Mochly-Rosen, D., et al., *J. Biol. Chem.*, 226:1466-1468 (1991a); Mochly-Rosen, et al., 1995) or the RACK-binding site on PKC (Ron, et al., 1995; Johnson, et al., 1996a) are isozyme-specific translocation inhibitors of PKC that selectively inhibit the function of the enzyme in vivo. For example, an eight amino acid peptide derived from εPKC (peptide εV1-2; SEQ ID NO:1, Glu Ala Val Ser Leu Lys Pro Thr) is described in U.S. Pat. No. 6,165,977. The peptide contains a part of the RACK-binding site on εPKC and selectively inhibits specific εPKC-mediated functions in cardiac myocytes. This εPCK peptide has been shown to be involved in cardiac preconditioning to provide protection from ischemic injury. Prolonged ischemia causes irreversible myocardium damage primarily due to death of cells at the infarct site. Studies in animal models, isolated heart preparations and isolated cardiac myocytes in culture have demonstrated that short bouts of ischemia of cardiac muscle reduce such tissue damage in subsequent prolonged ischemia (Liu, Y., et al., *J. Mol. Cell. Cardiol.* 27:883-892 (1995); Hu, K. and Nattel, S., *Circulation* 92:2259-2265 (1995); Brew, E. C., et al., *Am. J. Physiol* 269(Heart Circ. Physiol. 38):H1370-H1378 (1995); Schultz, J. E. J., et al., *Circ. Res.* 78:1100-1104 (1996)). This protection, which occurs naturally following angina and has been termed preconditioning, can be mimicked by a variety of non-specific PKC agonists (Mitchell, M. B., et al., *Circulation* 88:1633 (1993); Mitchell, M. B., et al., *Circ. Res.* 76:73-81 (1995); Murry, C. E., et al., *Circulation* 74:1123-1136 (1986); Speechly-Dick, M. E., et al., *Circ. Res.* 75:586-590 (1993)). Both δPKC and εPKC activation occurs following preconditioning (Gray, M. O. et al., *J. Biol. Chem.* 272: 30945-3095 (1997)), however, εPKC activation is required for protection of cardiac myocytes from ischemia-induced cell death (U.S. Pat. No. 6,165,977).

In a recent study, an εPKC-selective peptide agonist was shown to provide cardio-protection from ischemia when administered intracellulary to isolated neonatal and adult cardiomyocytes and when produced intracellulary in vivo in transgenic mice (Dorn, G., *Proc. Natl. Acad. Sci. USA* 96(22): 12798-12803 (1999)).

The ability of δPCK peptide agonists and antagonists to protect cells and tissue from an ischemic event or to reverse or reduce damage caused by an ischemic event has not been reported. More particularly, it is unknown in the art whether or not δPCK peptide agonists and antagonists can be delivered extracellulary to whole tissue or intact organs in vivo to achieve a therapeutic effect.

SUMMARY OF THE INVENTION

Accordingly, it is an object of the invention to provide a method of protecting tissue from damage due to an ischemic event.

It is a further object of the invention to provide a method of administering an δPKC peptide antagonist for protection of cells and tissue from damage due to an ischemic event.

It is yet another object of the invention to provide a method of ameliorating damage to tissue caused by an ischemic event.

It is still a further objective of the invention to provide a method of reducing or protecting cells and tissue from damage as a result of stroke.

It is another objective of the invention to provide a method of enhancing cellular or tissue damage as a result of an ischemic or hypoxic event.

In one aspect, the invention includes a peptide selected δV1-1 (SEQ ID NO:4), δV1-2 (SEQ ID NO:5), ψδRACK (SEQ ID NO:6), δV1-5 (SEQ ID NO:7), and derivatives and fragments thereof. Exemplary derivatives of δV1-1 are identified as SEQ ID NOS:34-48. Exemplary derivatives of δV1-2 are identified as SEQ ID NOS:65-71. Exemplary derivatives of ψδRACK are identified as SEQ ID NOS:11-19, 22-33. Exemplary fragments of δV1-1 are identified as SEQ ID NOS:49-64. Exemplary fragments of ψδRACK are identified as SEQ ID NO:20 and SEQ ID NO:21.

In one embodiment, the peptide is recombinantly produced, such as where the peptide is encoded by a polynucleotide. In other embodiments, the peptide is chemically synthesized.

In one embodiment, the peptide is linked to a moiety effective to facilitate transport across a cell membrane. Exemplary moieties include a Tat-derived peptide, an Antennapedia carrier peptide, and a polyarginine peptide.

In another embodiment, the peptide is joined to a second peptide to form a fusion peptide.

In another aspect, the invention includes a method of reducing ischemic injury to a cell or a tissue exposed to hypoxic conditions by administering to the cell or tissue an amount of an isozyme-specific δPKC antagonist. Contemplated antagonists include δV1-1 (SEQ ID NO:4), δV1-2 (SEQ ID NO:5), δV1-5 (SEQ ID NO:7), and derivatives and fragments thereof.

In various embodiments of this method, the peptide is administered prior to, during or after exposing the cell or tissue to said hypoxic conditions. The peptide can be linked to a carrier peptide, as described above.

In one embodiment, the peptide is administered by infusion through coronary arteries to an intact heart.

In another aspect, the invention includes a method of reducing or preventing or ameliorating damage to a cell or tissue due to stroke by administering to the cell or tissue an amount of an isozyme-specific δPKC antagonist. Contemplated antagonists include δV1-1 (SEQ ID NO:4), δV1-2 (SEQ ID NO:5), δV1-5 (SEQ ID NO:7), and derivatives and fragments thereof.

In various embodiments of this method, the peptide is administered prior to, during or after the stoke, when the cell or tissue is exposed to a hypoxic event. The peptide can be linked to a carrier peptide, as described above.

In another aspect, the invention includes a method of enhancing damage to a cell exposed to hypoxic conditions by administering to the cell an amount of an isozyme-specific δPKC agonist. Contemplated agonists include ψδRACK identified as SEQ ID NO:6, derivatives and fragments or ψδRACK. Exemplary derivatives include peptides identified as SEQ ID NOS:11-19, and SEQ ID NOS:22-29. Exemplary fragments include the peptides identified as SEQ ID NOS: 20-21.

In one embodiment, the peptide is administered to a tumor cell. The agonist peptide can be linked to a moiety effective to facilitate transport across a cell membrane.

In another aspect, the invention includes a method of identifying a compound effective to induce protection of a cell from hypoxic or ischemic damage. In the method, a δPKC peptide containing a δRACK binding site is contacted with a δPKC antagonist peptide with the δRACK binding site in the presence and absence of said test compound. The test compound is identified as being effective to induce protection if (i) binding in the presence of the test compound is decreased relative to binding in the absence of the test compound, or (ii) catalytic activity of the test compound is increased relative to activity in the absence of the test compound.

In this method, the δPKC peptide can be selected from the group consisting of δV1-1 (SEQ ID NO:4), δV1-2 (SEQ ID NO:5), δV1-5 (SEQ ID NO:7), and fragments and derivatives thereof.

In another aspect, the invention includes a method of identifying a compound effective to enhance hypoxic or ischemic damage in a cell. A ψδRACK agonist peptide is contacted with a δPKC peptide containing a RACK binding site in the presence and absence of a test compound. The test compound is identified as being effective to enhance ischemic damage if (i) binding in the presence of the test compound is decreased relative to binding in the absence of the test compound, or (ii) the catalytic activity of the δPKC in the presence of the test compound is increased relative to the catalytic activity in the absence of the test compound.

In one embodiment, a ψδRACK peptide selected from the group consisting of SEQ ID NO:6, fragments, and derivatives thereof is used. Exemplary suitable derivatives and fragments are identified in SEQ ID NOS:11-29.

In another aspect, the invention includes a method of providing protection to tissue from damage caused by an ischemic or hypoxic event by administering to the tissue a peptide selected from the group consisting of SEQ ID NO:4, SEQ ID NO:5, SEQ ID NO:7, derivatives and fragments thereof. Suitable derivatives and fragments include those given above.

In one embodiment, the peptide is administered by the intraveneous, parenteral, subcutaneous, inhalation, intranasal, sublingual, mucosal, and transdermal route. In another method, the peptide is administered during a period of reperfusion; that is, after a period of initial perfusion.

Protection against ischemia is provided to a variety of tissues, including but not limited to the brain, heart, eye, and kidney.

These and other objects and features of the invention will be more fully appreciated when the following detailed description of the invention is read in conjunction with the accompanying drawings.

BRIEF DESCRIPTION OF THE DRAWINGS

FIG. 1 shows the alignment of the primary sequence of rat δPKC (SEQ ID NO:2 from residue 1 to 123) and mouse θPKC (SEQ ID NO:3 from residue 1 to 124) V1 domains. The bracketed areas designated as δV1-1 (SEQ ID NO:4), δV1-2 (SEQ ID NO:5), and ψδR (SEQ ID NO:6) indicate regions of difference between the two isozymes.

FIGS. 7A-7B show the functional recovery of a working heart perfused with δV1-1 (FIG. 7A) or left untreated (FIG. 7B) after 20 minutes of global ischemia, where the left ventricle developed pressure (LVP, in mmHg), its first derivative (dP/dt, in mmHg/sec), and the coronary perfusion pressure (PP, in mmHg) are shown. On the right, an expanded trace of the same functional measurement are shown before (base line) and 30 minutes after reperfusion.

FIGS. 11A-11B are digitized photographs of brains taken from untreated animals (FIG. 11A) and animals treated with δV1-1 (FIG. 11B) prior to an induced stroke.

BRIEF DESCRIPTION OF THE SEQUENCES

Figure 2A:
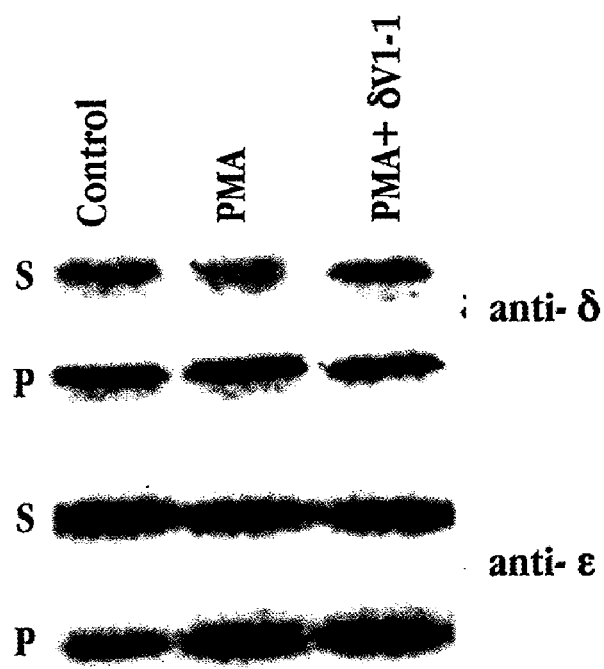
FIG. 2A shows a Western blot autoradiogram of soluble (S) and particulate (P) cell fractions after treatment with δV1-1 in the presence and absence of phorbol 12-myristate 13-acetate (PMA) and probing with anti-δPKC and anti-δPKC antibodies.

SEQ ID NO:1 is an eight amino acid peptide derived from εPKC, referred to as εV1-2 and described in U.S. Pat. No. 6,165,977.

SEQ ID NO:2 corresponds to amino acids 1-141 from the V1 domain of rat δPKC (accession no. KIRTCD).

SEQ ID NO:3 corresponds to amino acids 1-124 of V1 domain of mouse θPKC (accession no. Q02111).

SEQ ID NO:4 is an amino acid sequence from the first variable region of δPKC (amino acids 8-17), δV1-1.

SEQ ID NO:5 is an amino acid sequence from the first variable region of δPKC (amino acids 35-44), δV1-2.

SEQ ID NO:6 is an amino acid sequence from δPKC (amino acids 74-81), and is referred to herein as "pseudo-delta" RACK, or ψδRACK.

SEQ ID NO:7 is an amino acid sequence from a region of δPKC (amino acids 619-676), referred to herein as δV1-5.

SEQ ID NO:8 is the *Drosophila* Antennapedia homeodomain-derived carrier peptide.

SEQ ID NO:9 is a Tat-derived carrier peptide (Tat 47-57).

SEQ ID NO:10 is a βPKC-selective activator peptide.

SEQ ID NO:11 is a modification of SEQ ID:NO 6 (ψδRACK).

SEQ ID NO:12 is a modification of SEQ ID:NO 6 (ψδRACK).

SEQ ID NO:13 is a modification of SEQ ID:NO 6 (ψδRACK).

SEQ ID NO:14 is a modification of SEQ ID:NO 6 (ψδRACK).

SEQ ID NO:11 is a modification of SEQ ID:NO 6 (ψδRACK).

SEQ ID NO:16 is a modification of SEQ ID:NO 6 (ψδRACK).

SEQ ID NO:17 is a modification of SEQ ID:NO 6 (ψδRACK).

SEQ ID NO:18 is a modification of SEQ ID:NO 6 (ψδRACK).

SEQ ID NO:19 is a modification of SEQ ID:NO 6 (ψδRACK).

SEQ ID NO:20 is a fragment of SEQ ID:NO 6 (ψδRACK).

SEQ ID NO:21 is a fragment of SEQ ID:NO 6 (ψδRACK).

SEQ ID NO:22 is a modification of SEQ ID:NO 6 (ψδRACK).

SEQ ID NO:23 is a modification of SEQ ID:NO 6 (ψδRACK).

SEQ ID NO:24 is a modification of SEQ ID:NO 6 (ψδRACK).

SEQ ID NO:25 is a modification of SEQ ID:NO 6 (ψδRACK).

SEQ ID NO:26 is a modification of SEQ ID:NO 6 (ψδRACK).

SEQ ID NO:27 is a modification of SEQ ID:NO 6 (ψδRACK).

SEQ ID NO:28 is a modification of SEQ ID:NO 6 (ψδRACK).

SEQ ID NO:29 is a modification of SEQ ID:NO 6 (ψδRACK).

SEQ ID NO:30 is a modification of SEQ ID:NO 6 (ψδRACK).

SEQ ID NO:31 is a modification of SEQ ID:NO 6 (ψδRACK).

SEQ ID NO:32 is a modification of SEQ ID:NO 6 (ψδRACK).

SEQ ID NO:33 is a modification of SEQ ID:NO 6 (ψδRACK).

SEQ ID NO:34 is a modification of SEQ ID:NO 4 (δV1-1).
SEQ ID NO:35 is a modification of SEQ ID:NO 4 (δV1-1).
SEQ ID NO:36 is a modification of SEQ ID:NO 4 (δV1-1).
SEQ ID NO:37 is a modification of SEQ ID:NO 4 (δV1-1).
SEQ ID NO:38 is a modification of SEQ ID:NO 4 (δV1-1).
SEQ ID NO:39 is a modification of SEQ ID:NO 4 (δV1-1).
SEQ ID NO:40 is a modification of SEQ ID:NO 4 (δV1-1).
SEQ ID NO:41 is a modification of SEQ ID:NO 4 (δV1-1).
SEQ ID NO:42 is a modification of SEQ ID:NO 4 (δV1-1).
SEQ ID NO:43 is a modification of SEQ ID:NO 4 (δV1-1).
SEQ ID NO:44 is a modification of SEQ ID:NO 4 (δV1-1).
SEQ ID NO:45 is a modification of SEQ ID:NO 4 (δV1-1).
SEQ ID NO:46 is a modification of SEQ ID:NO 4 (δV1-1).
SEQ ID NO:47 is a modification of SEQ ID:NO 4 (δV1-1).
SEQ ID NO:48 is a modification of SEQ ID:NO 4 (δV1-1).
SEQ ID NO:49 is a fragment of SEQ ID:NO 4 (δV1-1).
SEQ ID NO:50 is a modified fragment of SEQ ID:NO 4 (δV1-1).
SEQ ID NO:51 is a modified fragment of SEQ ID:NO 4 (δV1-1).
SEQ ID NO:52 is a modified fragment of SEQ ID:NO 4 (δV1-1).
SEQ ID NO:53 is a modified fragment of SEQ ID:NO 4 (δV1-1).
SEQ ID NO:54 is a modified fragment of SEQ ID:NO 4 (δV1-1).
SEQ ID NO:55 is a modified fragment of SEQ ID:NO 4 (δV1-1).
SEQ ID NO:56 is a modified fragment of SEQ ID:NO 4 (δV1-1).
SEQ ID NO:57 is a modified fragment of SEQ ID:NO 4 (δV1-1).
SEQ ID NO:58 is a fragment of V1-11.
SEQ ID NO:59 is a fragment of δV1-1.
SEQ ID NO:60 is a fragment of δV1-1.
SEQ ID NO:61 is a fragment of δV1-1.
SEQ ID NO:62 is a fragment of V1-1.
SEQ ID NO:63 is a fragment of δV1-1.
SEQ ID NO:64 is a fragment of δV1-1.
SEQ ID NO:65 is a modification of SEQ ID:NO 5 (δV1-2).
SEQ ID NO:66 is a modification of SEQ ID:NO 5 (δV1-2).
SEQ ID NO:67 is a modification of SEQ ID:NO 5 (δV1-2).
SEQ ID NO:68 is a modification of SEQ ID:NO 5 (δV1-2).
SEQ ID NO:69 is a modification of SEQ ID:NO 5 (δV1-2).
SEQ ID NO:70 is a modification of SEQ ID:NO 5 (δV1-2).
SEQ ID NO:71 is a modification of SEQ ID:NO 5 (δV1-2).
SEQ ID NO:72 is the sequence of Annexin V.

DETAILED DESCRIPTION OF THE INVENTION

I. Definitions

Unless otherwise indicated, all terms herein have the same meaning as they would to one skilled in the art of the present invention. Practitioners are particularly directed to *Current Protocols in Molecular Biology* (Ausubel, F. M. et al, John Wiley and Sons, Inc., Media Pa.) for definitions and terms of the art.

Abbreviations for amino acid residues are the standard 3-letter and/or 1-letter codes used in the art to refer to one of the 20 common L-amino acids.

A "conserved set" of amino acids refers to a contiguous sequence of amino acids that is conserved between members of a group of proteins. A conserved set may be anywhere from two to over 50 amino acid residues in length. Typically, a conserved set is between two and ten contiguous residues in length. For example, for the two peptides MKAAEDPM (SEQ ID NO:11) and MRAPEDPM (SEQ ID NO:14), there are 4 identical positions (EDPM; SEQ ID NO:20) which form the conserved set of amino acids for these two sequences.

"Conservative amino acid substitutions" are substitutions which do not result in a significant change in the activity (e.g., δV1-1 PKC activity) or tertiary structure of a selected polypeptide or protein. Such substitutions typically involve replacing a selected amino acid residue with a different residue having similar physico-chemical properties. For example, substitution of Glu for Asp is considered a conservative substitution since both are similarly-sized negatively-charged amino acids. Groupings of amino acids by physico-chemical properties are known to those of skill in the art.

"Peptide" and "polypeptide" are used interchangeably herein and refer to a compound made up of a chain of amino acid residues linked by peptide bonds. Unless otherwise indicated, the sequence for peptides is given in the order from the amino termiums to the carboxyl terminus.

Two amino acid sequences or two nucleotide sequences are considered homologous (as this term is preferably used in this specification) if they have an alignment score of >5 (in standard deviation units) using the program ALIGN with the mutation gap matrix and a gap penalty of 6 or greater (Dayhoff, M. O., in ATLAS OF PROTEIN SEQUENCE AND STRUCTURE (1972) Vol. 5, National Biomedical Research Foundation, pp. 101-110, and Supplement 2 to this volume, pp. 1-10.) The two sequences (or parts thereof) are more preferably homologous if their amino acids are greater than or equal to 50%, more preferably 70%, still more preferably 80%, identical when optimally aligned using the ALIGN program mentioned above.

A peptide or peptide fragment is "derived from" a parent peptide or polypeptide if it has an amino acid sequence that is identical or homologous to the amino acid sequence of the parent peptide or polypeptide.

"Ischemia" or an "ischemic event" refers to an insufficient supply of blood to a specific cell, tissue or organ. A consequence of decreased blood supply is an inadequate supply of oxygen to the organ or tissue (hypoxia). Prolonged hypoxia may result in injury to the affected organ or tissue.

"Anoxia" refers to a virtually complete absence of oxygen in the organ or tissue, which, if prolonged, may result in death of the cell, organ or tissue.

"Hypoxia" or a "hypoxic condition" intend a condition under which a cell, organ or tissue receive an inadequate supply of oxygen.

"Reperfusion" refers to return of fluid flow into a tissue after a period of no-flow or reduced flow. For example, in reperfusion of the heart, fluid or blood returns to the heart through the coronary arteries after occlusion of these arteries has been removed.

"Tissue" as used herein intends a whole organ, either in vivo or ex vivo, a fragment of an organ, or two or more cells.

The term "PKC" refers to protein kinase C, or C-kinase.

The term "RACK" refers to receptor for activated C-kinase.

II. δPKC Peptide Agonists and Antagonists

In one aspect, the invention includes peptides effective to activate δPKC and peptides effective to inhibit δPKC. The sequence of the RACK for δPKC is unknown as this RACK has not yet been identified. Thus, it is a challenge to identify δPKC-selective activator and inhibitor peptides in the absence of any information about the δRACK sequence. Further, the exact role of δPKC in response to ischemia is also not known in the art. It is known that δPKC, like εPKC, undergoes translocation on ischemic preconditioning in rat (Gray, M. O. et al.; Chen, C.-H. et al., $Proc. Natl. Acad. Sci. USA$ 96:12784-12789 (1999)). However, whether the δPKC translocation results in protection from ischemia or not has been unknown until the present invention.

In studies performed in support of the present invention to identify peptide sequences for activation and inhibition of δPKC, the sequence of δPKC was compared to the sequence of θPKC, since of the three other novel PKC isozymes, δPKC is most similar to θPKC with a 52% identity of amino acid sequence Osada, S.-I, et al., $Molec. Cell. Biol.$ 12:3930-393 (1992); Baier, G. et al., $J. Biol. Chem.$ 268:4997-5004 (1993)). It was also assumed that each PKC isozyme should interact with a different RACK. Since the first variable (V1) domain of δPKC contains the RACK-binding site (Johnson et al. 1996a) regions least similar to θPKC may be involved in RACK binding. FIG. 1 compares the sequences of the V1 domain of rat δPKC (SEQ ID NO:2; accession no. KIRTCD) and mouse θPKC V1 domain (SEQ ID NO:3, accession no. Q02111). Three regions in the V1 domain of δPKC were identified with only 10% identity to θPKC. These regions are indicated in FIG. 1 by the bars above the sequence of δPKC and are referred to herein as δV1-1 having a sequence identified herein as SEQ ID NO:4 (SFNSYELGSL), δV1-2 having a sequence identified herein as SEQ ID NO:5 (ALTTDRGKLV), and ψδRACK having a sequence identified herein as SEQ ID NO:6 (MRAAEDPM). Not shown in FIG. 1 is yet another sequence identified from the δPKC sequence for testing of its activation or inhibition of δPKC. This sequences is identified as SEQ ID NO7 and is referred to herein as δV1-5.

As described in Example 1, the δV1-1 and ψδRACK peptides were analyzed to determine whether the peptides had activity, and if so, whether the activity was as an agonist or an antagonist of δPKC. As will be shown, δV1-1, δV1-2 and δV1-5 are δPKC antagonists and ψδRACK is a δPKC agonist. In these studies, the δV1-1 and ψδRACK peptides were modified with a carrier peptide by cross-linking via an N-terminal Cys-Cys bond to the $Drosophila$ Antennapedia homeodomain (SEQ ID NO:8; Théodore, L., et al., $J. Neurosci.$ 15:7158 (1995); Johnson, J. A., et al., $Circ. Res.$ 79:1086 (1996b)). In other studies, not described here, the peptide was modified with Tat (SEQ ID NO:9) or with polyarginine (Mitchell et al., $J. Peptide Res.$ 56:318-325 (2000); Rolhbard, et al., $Nature Med.,$ 6:1253-1257 (2000)) and gave results similar to those described herein. Details of the study are set forth in Example 1. In brief, the Antennapedia-conjugated peptides were introduced to cardiac cells at a concentration of 500 nM in the presence and absence of phorbol 12-myristate 13-acetate (PMA) or in the presence of each other. Translocation of δPKC isozyme was assessed by Western blot analysis cystosolic and particulate fractions of treated cells. Subcellular localization of δPKC isozyme was assessed by immunofluorescence by probing the blot with anti-δPKC, anti-αPKC, and anti-εPKC antibodies. Translocation was expressed as the amount of isozyme in the particulate fraction over the amount of isozyme in non-treated cells. The results are shown in FIGS. 2-4.

Figure 2B:
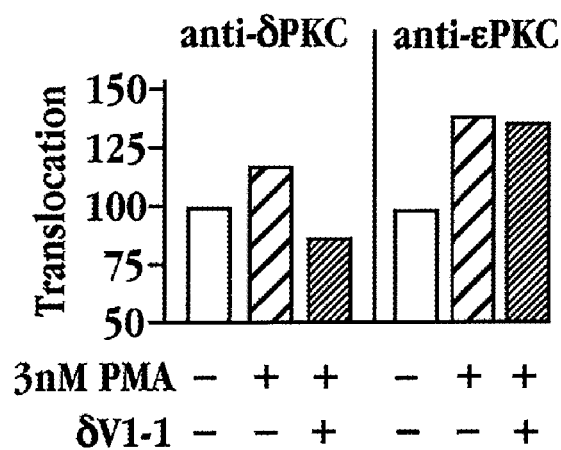
FIG. 2B shows the translocation of δPKC and εPKC, expressed as the amount of isozyme in the particulate fraction over the amount of isozyme in non-treated cells, for cells treated as indicated in FIG. 2A with δV1-1 in the presence (+) and absence (−) of PMA.

FIGS. 2A-2B show the results for the cells treated with δV1-1 in the presence (+) and absence (−) of PMA. FIG. 2A is the Western blot autoradiogram of soluble (S) and particulate (P) cell fractions after treatment with the peptide and after probing with anti-δPKC and anti-εPKC antibodies. FIG. 2B shows the translocation of δPKC expressed as the amount of isozyme in the particulate fraction over the amount of isozyme in non-treated cells. The δV1-1 peptide inhibited PMA-induced δPKC translocation. In other studies no shown here, the δV1-1 peptide did not inhibit the translocation of εPKC or αPKC.

Figure 3A:
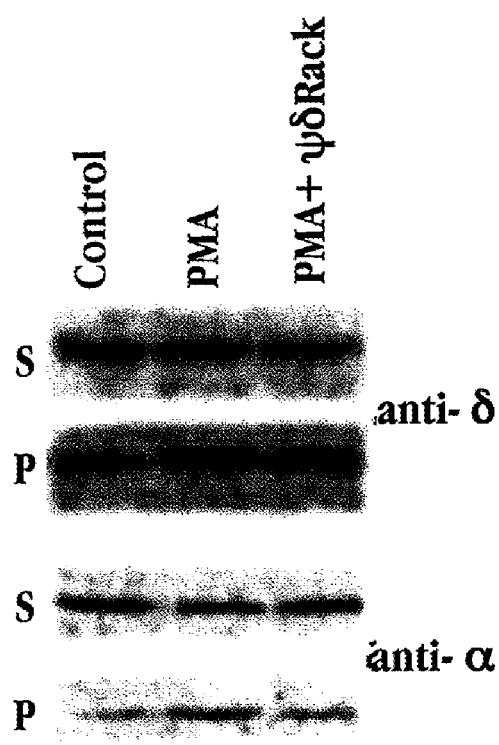
FIG. 3A shows a Western blot autoradiogram of soluble (S) and particulate (P) cell fractions after treatment with ψδRACK or with PMA and probing with anti-δPKC and anti-αPKC antibodies
Figure 3B:
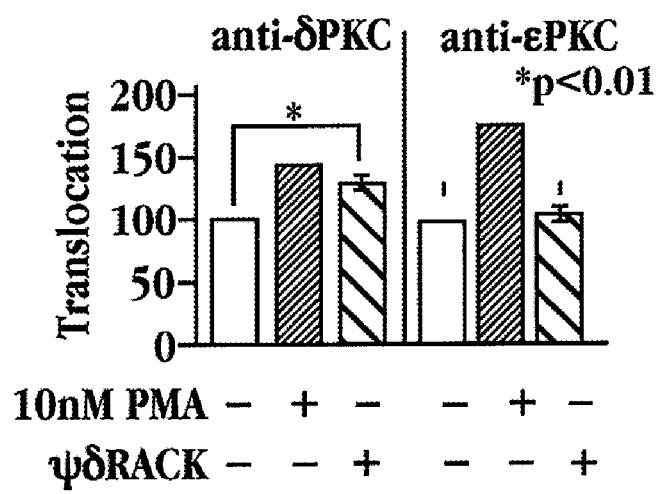
FIG. 3B shows the translocation of δPKC and αPKC, expressed as the amount of isozyme in the particulate fraction over the amount of isozyme in non-treated cells, for cells treated as indicated in FIG. 3A with ψδRACK in the presence (+) and absence (−) of PMA.

FIGS. 3A-3B are similar plots for the cells treated with ψδRACK in the presence (+) and absence (−) of PMA, WRACK was opposite in effect from δV1-1 in that it selectively induced δPKC translocation in cardiac myocytes, without affecting the translocation of PKCα or εPKC (not shown).

Figure 4A:
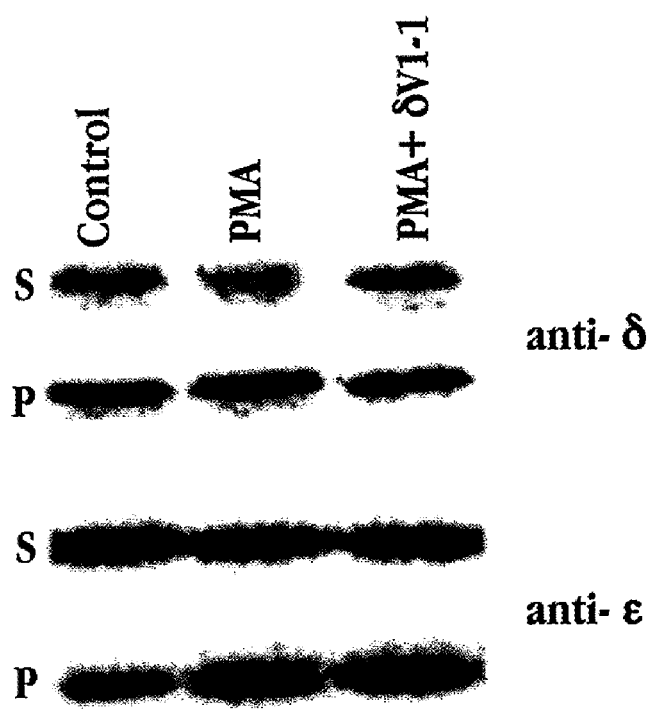
FIG. 4A shows a Western blot autoradiogram of soluble (S) and particulate (P) cell fractions after treatment with δV-1 in the presence and absence of ψδRACK and probing with anti-δPKC and anti-δPKC antibodies.
Figure 4B:
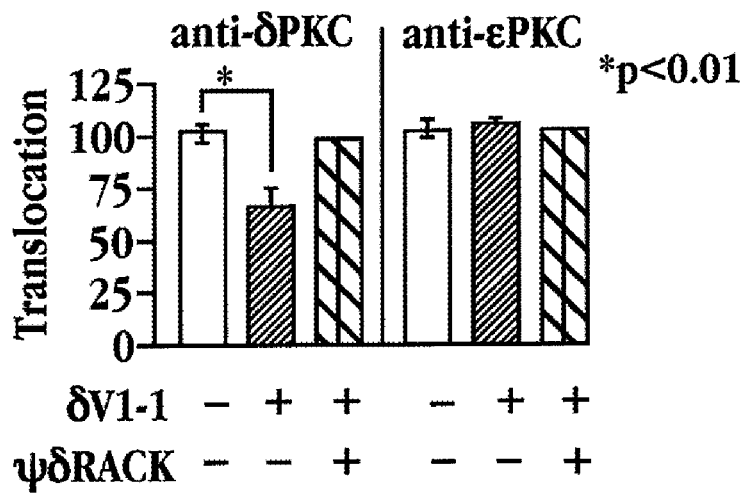
FIG. 4B shows the translocation of δPKC, expressed as the amount of isozyme in the particulate fraction over the amount of isozyme in non-treated cells, for cells treated as indicated in FIG. 4A with δV1-1 in the presence (+) and absence (−) of ΨδRACK.

FIGS. 4A-4B shows the results for the cells treated with δV1-1 in the presence and absence of ψδRACK. Basal partitioning of δPKC in the particulate fraction was inhibited by δV1-1 and the presence of ψδRACK reversed this δV1-1 effect.

Together the results in FIGS. 2-4 shows that SV1-1 is a selective translocation inhibitor of δPKC and that ψδRACK is analogous to the WRACK site and acts as a selective translocation activator of δPKC.

A. Protection of Cells from Damage Due to Ischemia

In another study, the δPKC activator peptide, ψδRACK, and the δPKC inhibitor peptide, δV1-1 were administered to isolated rat cardiac myocytes to determine the role of δPKC in protection from ischemia. As described in Example 2, the Antennapedia carrier-peptide conjugate of δV1-1 and/or ψδRACK was introduced into isolated adult rat cardiac myocytes ten minutes prior to prolonged ischemia. Cell damage was assessed using an osmotic fragility test by measuring uptake of trypan blue. The results are shown in FIGS. 5A-5C.

Figure 5A:
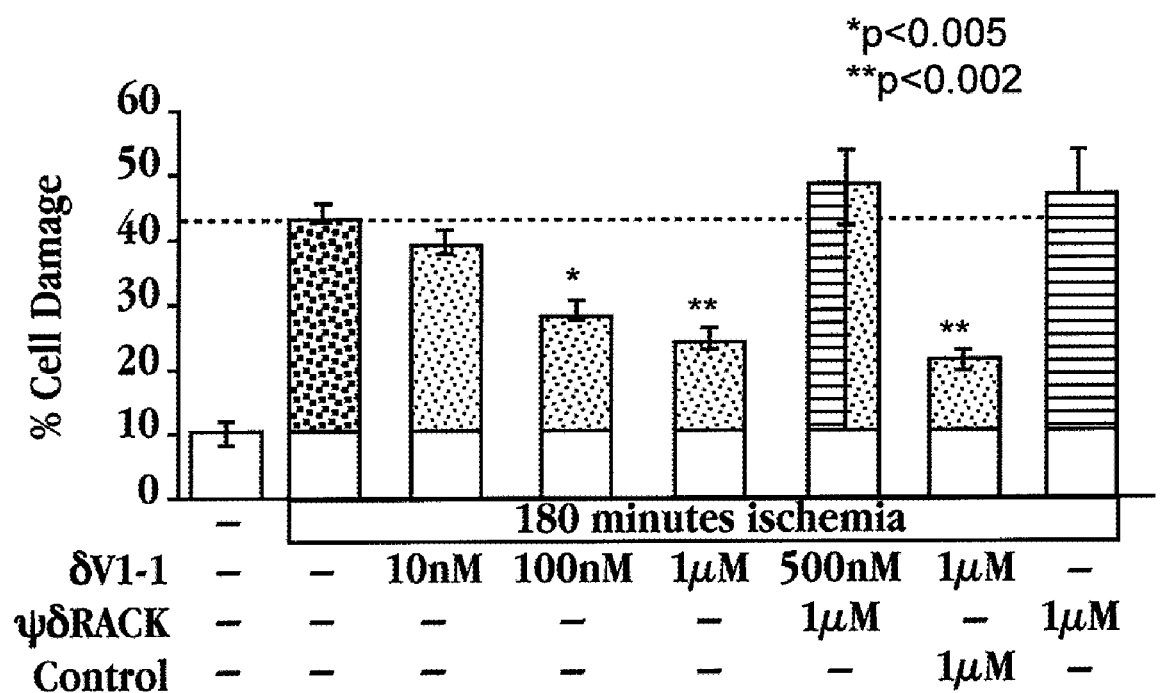
FIG. 5A shows percentage of cell damage for isolated cardiac myocytes treated with δV1-1 in the absence (−) or presence (in the concentrations indicated along the x-axis) of ψδRACK. The peptides were administered 10 minutes prior to a 180 minute ischemic period. As a control, βPKC-selective activator peptide was used.
Figure 5B:
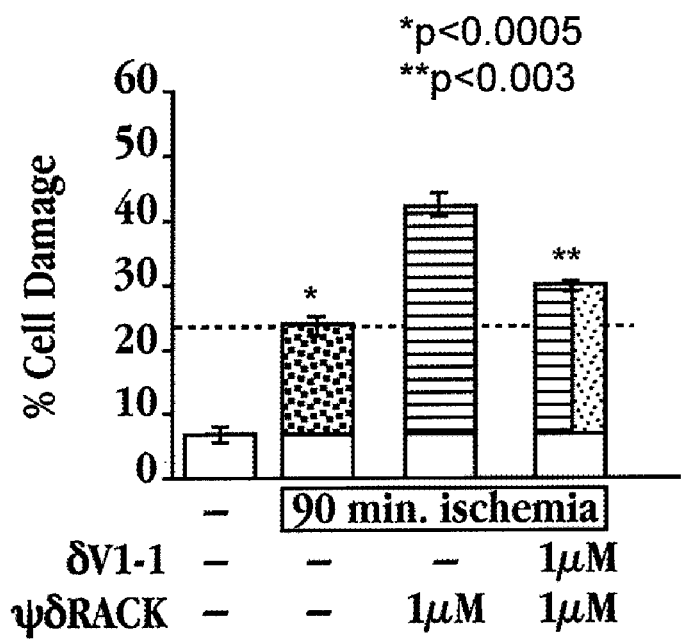
FIG. 5B shows percentage of cell damage for isolated cardiac myocytes treated with δV1-1 in the absence (−) or presence (in the concentrations indicated along the x-axis). The peptides were administered 10 minutes prior to a 90 minute ischemic period.

FIG. 5A shows the results for cells treated with δV1-1 at concentrations of 10 nM, 100 nM, 500 nM, and 1 μM in the presence or absence (−) of 1 μM ψδRACK. The results are presented as the percentage of cell damage for cells treated as indicated along the x-axis. As a control, a βPKC-selective activator peptide (SVEIWD, SEQ ID NO:10) was used. The peptides were administered ten minutes prior to the 180 minute ischemic period. The presence of δV1-1 administered prior to ischemia resulted in a concentration-dependent level of protection from ischemia-induced damage. The protection was prevented by co-incubation with the δPKC-specific translocation activator peptide, ψδRACK, but not with co-incubation with the control βPKC-selective translocation activator.

The data in FIG. 5A suggested that activation of δPKC with ψδRACK caused a slight increase in cardiac myocyte damage after an ischemic insult. Based on this, ψδRACK was hypothesized as acting synergistically with ischemia-induced activation of δPKC to cause cell damage. This was evaluated by reducing the period of ischemic insult, since synergism between ψδRACK and ischemia in inducing cell damage should become apparent when ischemic insult was reduced. Thus, another study was performed where the ischemic period was shortened to 90 minutes. The results of this study are shown in FIG. 5B. The ψδRACK-induced increase in cell damage became significant when the time of ischemia was shortened from 180 to 90 minutes, and was reversed by co-treatment with the δPKC inhibitor, δV1-1. Therefore, activation of δPKC by ischemia appears to mediate cell damage. Together, FIGS. 5A and 5B demonstrate that cell damage induced by simulated ischemia is due, at least in part, to activation of δPKC.

B. Ex Vivo Delivery of Peptides to Whole Hearts

In another study performed in support of the invention, the δPKC selective inhibitor peptide, δV1-1, or the activator peptide, ψδRACK, were delivered to whole hearts ex vivo to determine if the peptides have activity when introduced extracellulary to a whole organ. As described in Example 3, δV1-1 and ψδRACK peptides were conjugated to a carrier peptide, a Tat-derived peptide. The peptides were delivered into Langendorff perfused rat hearts prior to induction of an ischemic period. After perfusion with the peptides, global ischemia was effected for 30 minutes. After the 30 minute ischemic period, the amount of creatine phosphokinase (CPK) released was monitored during a 30 minute reperfusion period. The results are shown in FIGS. 6A-6B.

Figure 6A:
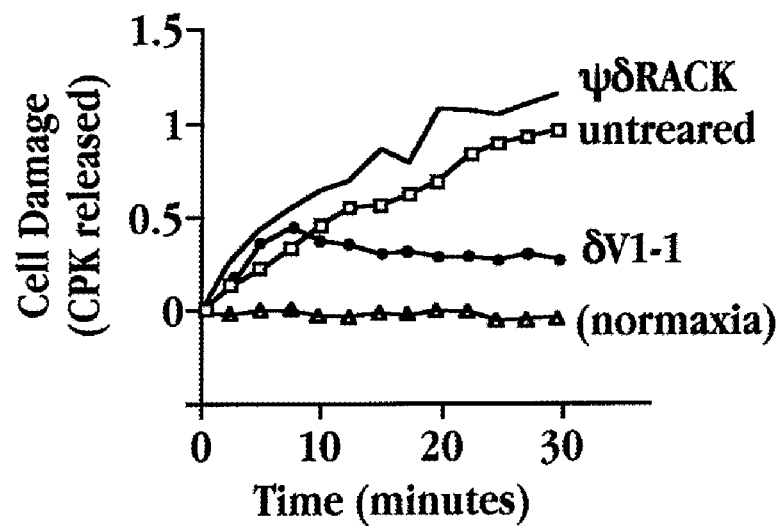
FIG. 6A shows the cell damage, as measured by creatine phosphokinase (CPK) release in whole rat hearts treated ex vivo with δV1-1 (solid circles) or with ψδRACK (solid diamonds) as a function of time post-ischemia and post-treatment. As controls, some hearts were left untreated prior to ischemia (open squares) and other hearts were maintained in normoxia conditions (open triangles).

FIG. 6A shows the cell damage, as measured by creatine phosphokinase (CPK) release in the whole rat hearts treated with δV1-1 (solid circles) or with ψδRACK solid diamonds) as a function of time during the post-ischemia, reperfusion period. As controls, some hearts were left untreated prior to ischemia (open squares) and other hearts were maintained in normoxia conditions (open triangles).

Figure 6B:
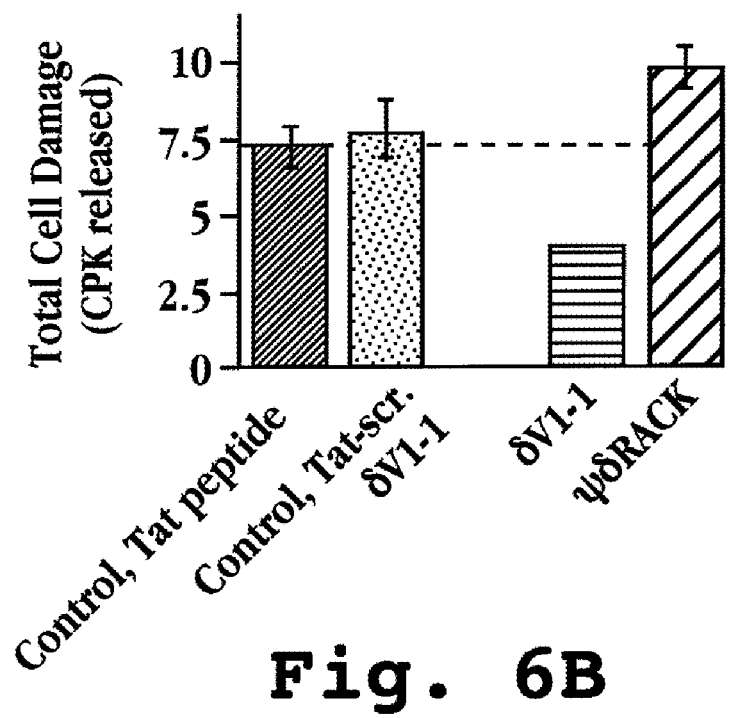
FIG. 6B is a bar graph showing the total cell damage, as measured by total CPK release for the ex vivo hearts treated as described in FIG. 6A with δV1-1 and with ψδRACK, as well as ex vivo hearts treated with two controls: the Tat-carrier peptide alone and with a scrambled δV1-1 sequence conjugated to Tat-carrier peptide.

FIG. 6B is a bar graph showing the total cell damage, as measured by total CPK release for the ex vivo hearts treated as described in FIG. 6A with δV1-1 and ψδRACK. FIG. 6B also shows the total cell damage for ex vivo hearts treated with two controls: the Tat-carrier peptide alone and with a scrambled ψδRACK sequence conjugated to Tat-carrier peptide.

FIGS. 6A-6B show that acute administration of the δPKC activator, ψδRACK, enhanced cardiac damage induced by ischemia by about 30%. Acute administration of the δPKC-selective inhibitor, δV1-1, protected hearts against ischemic damage as shown by decreased release of creatine kinase. Together, these data indicate that in an intact heart, inhibition of δPKC conferred greater than 50% protection against ischemic damage (FIG. 6A). Accordingly, the invention contemplates a method of protecting a cell or a tissue from damage due to ischemia by administering a δPKC-selective antagonist, such as δV1-1, δV1-2, δV1-5, to the tissue. Such administration is effective to reduce cell damage by at least about 10%, more preferably by at least about 25%, and most preferably by at least about 50% when compared to tissue left untreated prior to an ischemic insult.

Another study was performed to determine if the peptides could be delivered to an intact organ to provide protection after an ischemic insult. In this study, as described in Example 4, the rat heart model described above was used and the hemodynamic parameters were measured during the 20 minutes of global ischemia and the 20 minutes of reperfusion. During the reperfusion only, δV1-1 was delivered at a concentration of 500 nM. The results are shown in FIGS. 7A-7B.

FIG. 7A shows the functional recovery of a working heart perfused with δV1-1 after 20 minutes of global ischemia, where the left ventricle developed pressure (LVP, in mmHg), its first derivative (dP/dt, in mmHg/sec), and the coronary perfusion pressure (PP, in mmHg) are shown. FIG. 7B is a similar plot for an untreated heart. As seen by comparing the traces for the δV1-1 treated heart (FIG. 7A) and the untreated heart FIG. 7B), when δV1-1 was delivered during the first 20 minutes of reperfusion, there was a significant improvement in functional recovery after ischemia. In particular, a significant improvement in both the LVP recovery and its first derivative (dP/dt) were achieved by administering δV1-1 after ischemic insult. The δV1-1 peptide reduced the elevated LVP end diastolic pressure and the coronary perfusion pressure (PP). In addition there was a ~50% reduction in creatine phosphokinase release as compared with hearts treated with vehicle control (not shown).

In a similar study, five pairs of rats were treated as described in Example 4, where the ex vivo hearts were subjected to 20 minutes of ischemia and 30 minutes of reperfusion. During the first 20 minutes of reperfusion, 500 nM of δV1-1 or vehicle control was administered. The averaged results are shown in FIGS. 8A-8C.

Figure 8A:
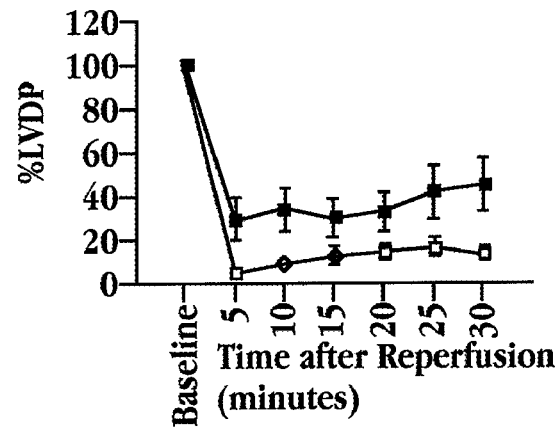
FIGS. 8A-8C are plots of percent of left ventricular developed pressure (% LVDP, FIG. 8A), end diastolic pressure (EDP, FIG. 8B) and perfusion pressure (PP, FIG. 8C) of a working heart as a function of time before ischemia (baseline) and 5 to 30 minutes after ischemia and during treatment δV1-1 (closed squares) or untreated (open circles).

FIG. 8A shows the percent of left ventricular developed pressure (% LVDP) before ischemia, noted on the x-axis as "baseline" and during the 5-30 minute period after reperfusion was provided. Data were collected during the reperfusion, meaning during and after treatment with δV1-1. Hearts treated with the δV1-1 peptide (closed squares) had a 2-fold to 4-fold higher LVDP than hearts left untreated (open circles).

Figure 8B:
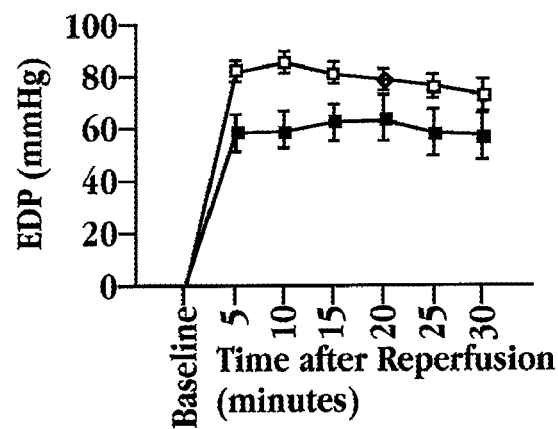

FIG. 8B is a similar plot showing the end diastolic pressure (EDP) before ischemia, noted as "baseline" on the x-axis, and during the 5-30 minute period after reperfusion treatment with δV1-1 (closed squares) or after reperfusion with a control vehicle (open circles). The EDP for hearts treated with δV1-1 was approximately 60 mmHg. Hearts left untreated after ischemia (open circles) had an EDP of between about 70-80 mmHg.

Figure 8C:
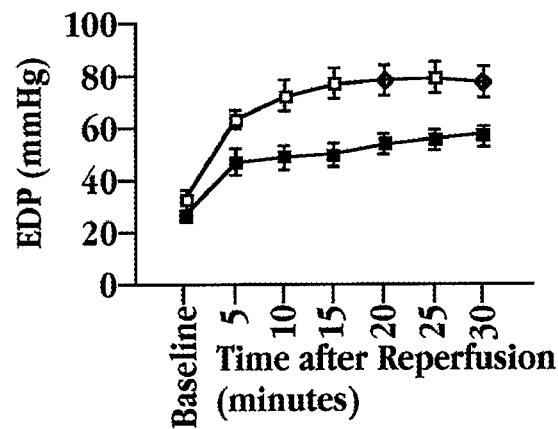

FIG. 8C shows the perfusion pressure (PP) of the δV1-1 treated hearts (closed squares) and the untreated hearts (open circles). The baseline perfusion pressure before ischemia is indicated on the x-axis. After ischemia and after treatment with δV1-1 the perfusion pressure was about 75% of that found hearts left untreated.

The data in FIGS. 7-8 show that administration of a δPKC antagonist peptide, such as δV1-1, δV1-2, δV1-5, after an ischemic insult to a cell or tissue is effective to protect the cell or tissue from damage du to ischemia and resulting hypoxia. The data also show that a δPKC antagonist peptide is effective to reduce or minimize the damage due to ischemia and hypoxia allowing the tissue to recover its functional properties following ischemia.

C. In Vivo Treatment with δV1-1

In another study in support of the invention, the ability of δV1-1 peptide to protect tissue from damage due to an ischemic or hypoxic event was evaluated by administering the peptide in vivo to adult female pigs. As detailed in Example 5, δV1-1 peptide was administered to the pigs during the last 10 minutes of a 30 minute ischemic insult. Five days later, the hearts were analyzed for tissue damage. The results are shown in FIGS. 9A-9B.

Figure 9A:
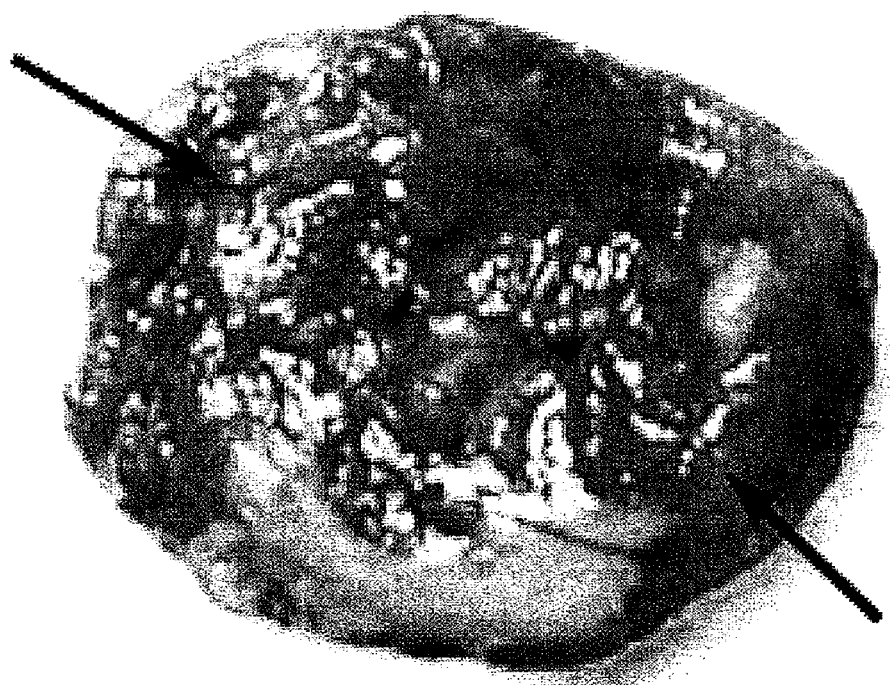
FIGS. 9A-9B are photos obtained by a digital camera of pig heart slices taken from the pigs five days after treatment in vivo with δV1-1 (FIG. 9A) or with the carrier peptide alone as a control (FIG. 9B) during the last 10 minutes of a 30 minute ischemic insult.
Figure 9B:
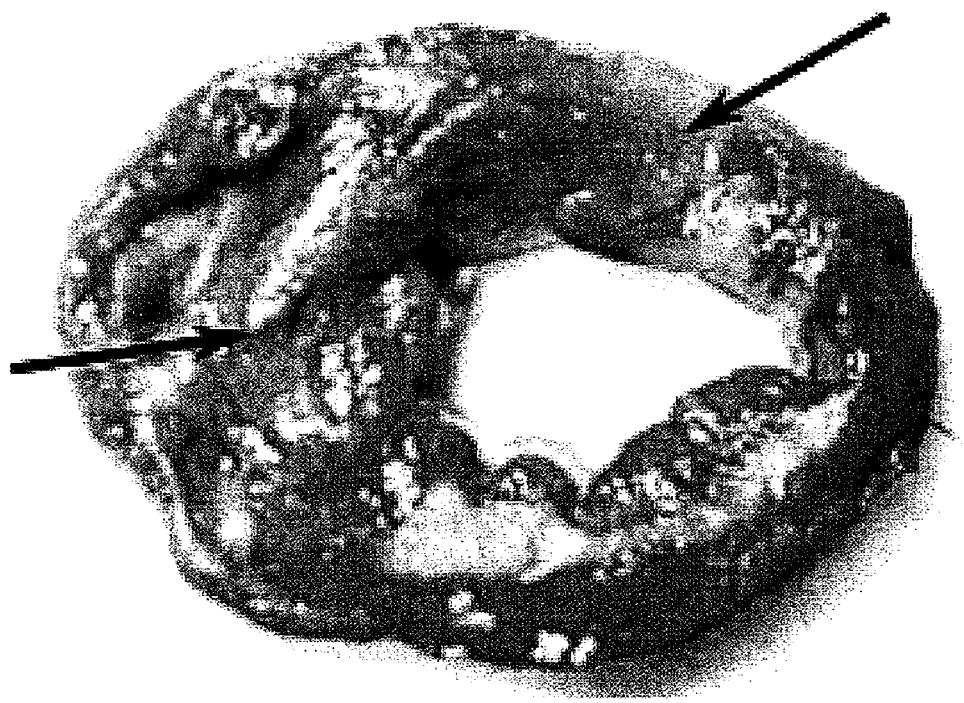

FIGS. 9A-9B are digitized photos of pig heart slices taken from the pigs treated in vivo five days earlier with δV1-1 (FIG. 9A) or with the carrier peptide alone as a control (FIG. 9B). The hearts were stained with a double-staining technique (Example 5) that allowed determination of the area at risk for ischemic injury (area within the arrows, mainly in the lower hemisphere between the two arrows) and infarcted area (white area in FIG. 9B). As seen in FIG. 9B, control hearts have a large infarct area within the area at risk (borders shown with arrows). In contrast, pigs that received the δV1-1 peptide (FIG. 9A) have a significantly reduced infarct area. The white area in FIG. 9A that is outside the area of risk (outside the arrows) is connective tissue and fat, and is not an infarcted area.

Figure 9C:
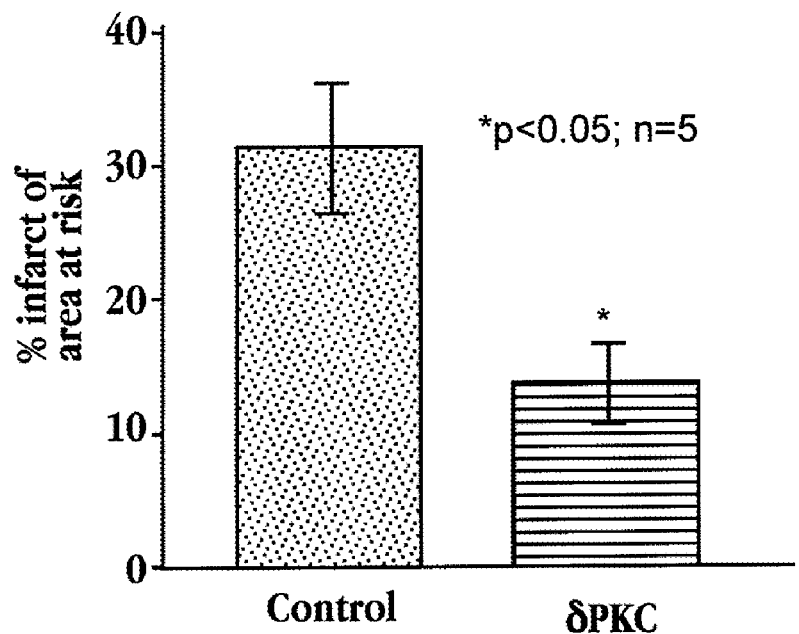
FIG. 9C is a bar graph showing the percent of infarct of the area at risk determined from the heart slices of FIGS. 9A-9B, for the pigs treated with δV1-1 and for the untreated, control animals.

FIG. 9C is a bar graph showing the percent of infarct of the area at risk for the untreated, control animals and the animals treated with V1-1. Animals treated with a δPKC antagonist had a nearly two-fold lower percentage of infarct than animals left untreated. Together, FIGS. 9A-9C show that δV1-1 can be administered in vivo to a whole organ and provide protection from damage due to ischemia.

Blood samples and tissue samples of lung, liver, brain, gut, kidney, etc. were collected from the animals and analyzed at a pathology lab. All samples were normal and no inflammation or tissue abnormalities were observed. In addition, there was no adverse effect of two injections of the δV1-1 antagonist peptide at 1 μM final concentration in the mouse model. Kidney, liver, brain, and lung functions were normal and all blood analyses were also normal.

Figure 10:
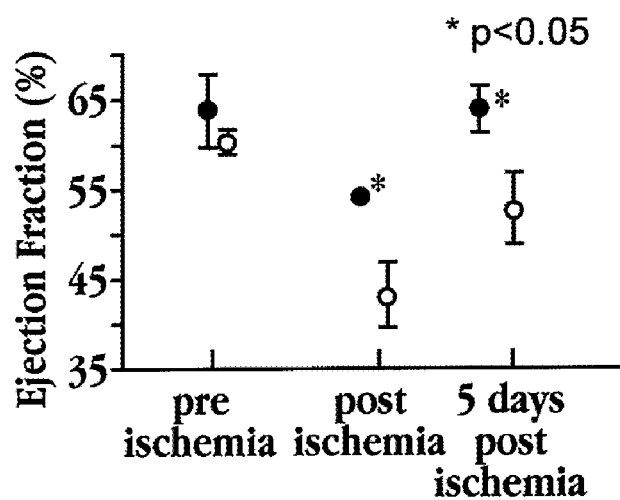
FIG. 10 is a graph showing the ejection fraction, as measured by left ventricurogram in pigs at three time points: (1) before occlusion of left anterior descending artery by balloon catheter (pre ischemia); (2) immediately after reperfusion with δV1-1 (post ischemia); and (3) before sacrifice five days later (5 days post ischemia), for animals treated with δV1-1 (solid circles) and for control animals treated with a scrambled peptide (open circles).

In another study, left ventricurogram was performed in pigs (n=5) at three time points. (1) before occlusion of left anterior descending artery by balloon catheter (pre ischemia); (2) immediately after reperfusion with 2.5 μM/10 mL of δV1-1 (post ischemia); and (3) before sacrifice five days later (5 days post ischemia), using 6 Fr. of pig-tail catheter. LVG was recorded by 2 views, right anterior oblique and left anterior oblique. Ejection fraction (EF), the percent of blood ejected in a beat, during maximum contraction, of the total maximum present in the left ventricle, was analyzed by the software, Plus Plus (Sanders Data Systems), and the averages of two views were evaluated. Ejection fractions were calculated based on left ventricle dimensions and the results are shown in FIG. 10. Ejection fraction is a measure of how well the heart is functioning, with a higher ejection fraction indicative of a better functioning heart. An ejection fraction of less than 50% in a short period of time can suggest progression into a state of heart failure. Animals treated with δV1-1 (solid circles) exhibited a less pronounced decrease in ejection fraction than did the control animals treated with a scrambled peptide (open circles), suggesting that the peptide is effective to reduce or prevent damage to the cells and tissue due to ischemia. This is also evident from the data point at five days post ischemia, where animals treated with δV1-1 had an ejection fraction on par with that measured prior to ischemia and significantly higher than the untreated animals.

In summary, the ex vivo and in vivo studies show that δV1-1, when delivered before, during, or after ischemia, confers a substantial reduction of damage to the heart and brain induced by ischemia. Therefore, treatment with a δPKC peptide antagonist, such as δV1-1, δV1-2, δV1-5 peptides, provides a therapeutic treatment for tissues exposed to ischemia, such as occurs during cardiac ischemia.

D. In Vivo Treatment for Inhibition of Stroke-Induce Damage

In another study performed in support of the invention, the ability of δV1-1 peptide (SEQ ID NO:4) to inhibit damage to the brain as a result of stroke was examined. In this study, described in Example 6, a rat cerebral ischemia model was used. Ischemia was induced using an intraluminal suture to occlude the ostium of the middle cerebral artery. δV1-1 conjugated to Tat peptide (SEQ ID NO:9) or the Tat peptide alone were injected into the carotid artery before and after a two hour occlusion period. The brain from each animal was harvested 24 hours later, stained, and examined. The results are shown in FIGS. 11A-11B.

FIG. 11A is a digitized photograph of brains taken from untreated animals subjected to an induced stroke. The stained rat brain sections clearly demonstrated a middle cerebral artery territory infarct. The infarct area induced by the two hours of occlusion was reproducible between animals. FIG. 11B shows the brain sections from two animals treated with δV1-1 peptide prior to ischemia and at the end of the ischemic period. The significant reduction in infarct area is readily apparent.

Accordingly, the invention contemplates a method of reducing damage to tissue in the central nervous system, such as the brain, neurons, and glial cells, by administering a δPKC peptide antagonist, such as δV1-1, δV1-2, or δV1-5, prior to, during, or after a stroke. The peptide is effective to reduce the tissue damage, as evidenced by at least about a 10% reduction in infarct area, more preferably at least about a 25% reduction, and most preferably, at least about a 50% reduction in infarct area, when compared to untreated tissue exposed to the ischemic insult.

III. Method of Use

As described above, the peptides of the invention, δV1-1, δV1-2, δV1-5, and ψδRACK, act as translocation inhibitors or activators of δPKC. ψδRACK is an agonist, inducing translocation of δPKC to promote cell damage due to ischemia and/or hypoxia. δV1-1, δV1-2, and δV1-5 are antagonists, inhibiting δPKC translocation to prevent cell damage due to ischemia and resulting hypoxia.

It will be appreciated that the peptides can be used in native form or modified by conjugation to a carrier, such as those described above. Alternatively, one or two amino acids from the sequences can be substituted or deleted and exemplary modifications and derivatives and fragments for each peptide are given below.

For the ψδRACK peptide, identified as SEQ ID NO:6, potential modifications include the following changes shown in lower case: MkAAEDPM (SEQ ID NO:11), MRgAEDPM (SEQ ID NO:12), MRAgEDPM (SEQ ID NO:13), MRApEDPM (SEQ ID NO:14), MRAnEDPM (SEQ ID NO:15), MRAAdDPM (SEQ ID NO:16), MRAAEDPv (SEQ ID NO:17), MRAAEDPi (SEQ ID NO:18), MRAAEDPI (SEQ ID NO:19), and MRAAEDmp (SEQ ID NO:22), MeAAEDPM (SEQ ID NO:23), MdAAEDPM (SEQ ID NO:24), MRAAEePl (SEQ ID NO:25), MRAAD-EDPl (SEQ ID NO:26), MRAAEePi (SEQ ID NO:27), MRAAEePv (SEQ ID NO:28), MRAAEDPv (SEQ ID NO:29), and any combination of the above. The following modifications to ψδRACK are also contemplated and are expected to convert the peptide from agonist to an antagonist: MRAAnDPM (SEQ ID NO:30), and MRAAqDPM (SEQ ID NO:31), MRAAEqPM (SEQ ID NO:32), MRAAEnPM (SEQ ID NO:33). Suitable fragments of ψδRACK are also contemplated, and SEQ ID NOS: 20, 21 are exemplary.

Accordingly, the term "a δPKC agonist" as used herein intends a ψδRACK peptide, which refers to SEQ ID NO:6 and to peptides having a sequence homologous to SEQ ID NO:6 and to peptides identified herein, but not limited to, as SEQ ID NO:11-19 and SEQ ID NO:21-29. The term a δPKC agonist further refers to fragments of these ψδRACK peptides, as exemplified by SEQ ID NOS:20-21.

For δV1-1, potential modifications include the following changes shown in lower case: tFNSYELGSL (SEQ ID NO:34), aFNSYELGSL (SEQ ID NO:35), SFNSYELGtL (SEQ ID NO:36), including any combination of these three substitutions, such as tFNSYELGtL (SEQ ID NO:37). Other potential modifications include SyNSYELGSL (SEQ ID NO:38), SFNSfELGSL (SEQ ID NO:39), SNSYdLGSL (SEQ ID NO:40), SFNSYELpSL (SEQ ID NO:41). Other potential modifications include changes of one or two L to I or V, such as SFNSYEiGSv (SEQ ID NO:42), SFNSYEvGSi, (SEQ ID NO:43) SFNSYELGSv (SEQ ID NO:44), SFN-SYELGSi (SEQ ID NO:45), SFNSYEiGSL (SEQ ID NO:46), SFNSYEvGSL (SEQ ID NO:47), aFNSYELGSL (SEQ ID NO:48), and any combination of the above-described modifications. Fragments and modification of fragments of δV1-1 are also contemplated, such as YELGSL (SEQ ID NO:49), YdLGSL (SEQ ID NO:50), fDLGSL (SEQ ID NO:51), YDiGSL (SEQ I, iGSL (SEQ ID NO:59)D NO:52), YDvGSL (SEQ ID NO:53), YDLpsL (SEQ ID NO:54), YDLgIL (SEQ ID NO:55), YdLGSi (SEQ ID NO:56), YdLGSv (SEQ ID NO:57), LGSL (SEQ ID NO:58), iGSL (SEQ ID NO:59), vGSL (SEQ ID NO:60), LpSL (SEQ ID NO:61), LGIL (SEQ ID NO:62), LGSi (SEQ ID NO:63), LGSv (SEQ ID NO:64).

Accordingly, the term "a δV1-1 peptide" as used herein refers to a peptide identified by SEQ ID NO:4 and to peptides homologous to SEQ ID NO:4, including but not limited to the peptides set forth in SEQ ID NOS:34-48, as well as fragments of any of these peptides that retain activity, as exemplified by but not limited to SEQ ID NOS:49-64.

For δV1-2, potential modifications include the following changes shown in lower case: ALsTDRGKTLV (SEQ ID NO:65), ALTsDRGKTLV (SEQ ID NO:66), ALTTDRGK-sLV (SEQ ID NO:67), and any combination of these three substitutions, ALTTDRpKTLV (SEQ ID NO:68), ALTTDRGrTLV (SEQ ID NO:69), ALTTDkGKTLV (SEQ ID NO:70), ALTTDkGkTLV (SEQ ID NO:71), changes of one or two L to I, or V and changes of V to I, or L and any combination of the above. In particular, L and V can be changed to V, L, I R and D, E can change to N or Q.

Accordingly, the term "a δV1-2 peptide" as used herein refers to a peptide identified by SEQ ID NO:5 and to peptides homologous to SEQ ID NO:5, including but not limited to the peptides set forth in SEQ ID NOS:65-71, as well as fragments of any of these peptides that retain activity.

For δV1-5 (SEQ ID NO:7), potential modifications include those similar to the modifications described for δV1-2. The term "a δV1-5 peptide" as used herein refers to SEQ ID NO:7 and to peptides homologous to SEQ ID NO:7 as well as fragments thereof that retain activity.

Accordingly, the term "a δPKC antagonist" as used herein intends a δPKC peptide, which refers to any a δV1-1 peptide, a δV1-2 peptide and a δV1-5 peptide.

In still other embodiments, the peptide can be part of a fusion protein or a transport protein conjugate. Typically, to form a fusion protein, the peptide is bound to another peptide by a bond other than a Cys-Cys bond. An amide bond from the C-terminal of one peptide to the N-terminal of the other is exemplary of a bond in a fusion protein. The second peptide to which the δPKC agonist/antagonist peptide is bound can be virtually any peptide selected for therapeutic purposes or for transport purposes. For example, it may be desirable to link the δV1-1 peptide to a cytokine or other peptide that elicites a biological response.

Where the peptide is part of a conjugate, the peptide is typically conjugated to a carrier peptide, such as Tat-derived transport polypeptide (Vives, et al. *J. Biol. Chem.*, 272: 16010-16017 (1997)), polyarginine (Mitchell et al., 2000; Rolhbard et al., 2000) or Antennapedia peptide by a Cys-Cys bond. See U.S. Pat. No. 5,804,604. In another general embodiment, the peptides can be introduced to a cell, tissue or whole organ using a carrier or encapsulant, such as a liposome in liposome-mediated delivery.

The peptide may be (i) chemically synthesized or (ii) recombinantly produced in a host cell using, e.g., an expression vector containing a polynucleotide fragment encoding said peptide, where the polynucleotide fragment is operably linked to a promoter capable of expressing mRNA from the fragment in the host cell.

In another aspect, the invention includes a method of reducing ischemic injury to a cell, tissue or whole organ exposed to hypoxic conditions. The method includes introducing into the cell, tissue or whole organ prior to exposure to hypoxic conditions, a therapeutically-effective amount of an isozyme-specific δPKC antagonist, such as δV1-1, δV1-2, δV1-5, or any of the modification, derivatives, and fragments of these peptides described above. The δPKC antagonist inhibits δPKC, resulting in protection of the cell, tissue or whole organ by reducing ischemic injury to the cell. The reduction of ischemic injury is measured relative to the ischemic injury suffered by a corresponding cell, tissue or whole organ that did not undergo δPKC antagonist peptide pretreatment.

It will be appreciated that the dose of peptide administered will vary depending on the condition of the subject, the timing of administration (that is, whether the peptide is administered prior to, during, or after an ischemic event). Those of skill in the art are able to determine appropriate dosages, using, for example, the dosages used in the whole organ and animal studies described herein.

The method can be practiced with a variety of cell types, including cardiac cells, central nervous system (CNS) cells (e.g., neurons, glial cells), kidney cells and the like. A variety of tissue or whole organs can be treated, including but not limited to the brain, heart, eye, and kidney.

The peptides can be administered to the cell, tissue or whole organ in vitro, in vivo, or ex vivo. All modes of administration are contemplated, including intraveneous, parenteral, subcutaneous, inhalation, intranasal, sublingual, mucosal, and transdermal. A preferred mode of administration is by infusion or reperfusion through arteries to a target organ, such as through the coronary arteries to an intact heart.

In yet another aspect, the invention includes a method of enhancing ischemic injury to a cell, tissue or whole organ exposed to hypoxic conditions. This method is relevant to, for example, the treatment of solid tumors in subjects. The method also finds use in in vitro or in vivo research where damage to a cell or tissue is desired. The method includes introducing into the cell, tissue or whole organ a therapeutically-effective amount of an isozyme-specific δPKC agonist, such as ψδRACK (SEQ ID NO:6) or any of the peptides obtained from a modification to ψδRACK as discussed above. The extent of enhanced ischemic injury is measured relative to the ischemic injury suffered by a corresponding cell, tissue or whole organ untreated with a δPKC agonist.

IV. Identification and Screening of Test Compounds

In another aspect, the invention includes methods of identifying compounds effective to induce protection of a cell or tissue from hypoxic/ischemic damage or to enhance hypoxic or ischemic damage in a cell or tissue.

In the first method, the δPKC-specific agonists δV1-1, δV1-2, δV1-5 or any of the modifications of these peptides described above, are used to identify compounds effective to inhibit δPKC translocation in cells and/or to competitively displace the peptide from Annexin V (SEQ ID NO:72) or other δRACK and/or to prevent or inhibit the peptide from binding to such a δRACK. Such compounds find use as therapeutic agents to inhibit δPKC translocation and/or function to thereby induce protection of cells or tissues from damage due to ischemia. The compounds also find use as screening tools to identify other peptides or compounds suitable for the same purpose.

In this method, a δPKC peptide containing a δRACK binding site, such as Annexin V, is brought into contact with a δPKC antagonist peptide with the δRACK binding site, such as δV1-1, δV1-2, or δV1-5, in the presence and absence of a test compound. The interaction of the test compound with the peptide having the δRACK binding site is monitored and/or the catalytic activity of the δPKC agonist or the test compound is monitored. Generally, the test compound is identified as being effective to induce protection from an ischemic or an hypoxic event if, in the presence of the test compound, binding of the peptide antagonist to the δRACK binding site is decreased, relative to binding in the absence of the test compound. Alternatively, the catalytic activity of the components can be monitored. For example, the phosphorylation activity of the peptides can be monitored. If the ability of the test compound to increase phosphorylation, or some other catalytic activity subsequent to binding, is increased relative to activity in the absence of the test compound then the compound is identified as being effective to induce protection from damage caused by either a hypoxic or an ischemic event.

In another method, the agonist peptide ψδRACK can be used to identify compounds effective to enhance hypoxic or ischemic damage in a cell or tissue. In this method, a ψδRACK agonist peptide is brought into contact with a δPKC peptide containing a δRACK binding site in the presence and absence of a test compound. The test compound, if able to decrease binding of the peptide agonist to the δRACK binding site relative to binding in the absence of the test compound, is identified as being effective to enhance damage due to ischemia. Suitable ψδRACK peptides include the peptide identified as SEQ ID NO:6, fragments, and derivatives thereof, including but not limited to those set forth in SEQ ID NOS:10-24.

ψδRACK-like compounds can also be identified by measuring its effect on the catalytic activity of δPKC in vitro. The desired compound will increase the catalytic activity of δPKC in the presence of limiting amounts of δPKC co-factors (Ron et al., 1995). Catalytic activity refers to the ability of the peptide to phosphorylate another protein or substrate.

Experimental details of a similar screening method are set forth in U.S. Pat. No. 6,165,977, and this portion on Col. 14, line 45-Col 15, line 54 is incorporated by reference herein. In brief, and by way of example for identifying a compound effective to protect a cell or tissue from ischemia, δPKC is immobilized inside the wells of a multiwell plate by introducing a solution containing δPKC into the plate and allowing the δPKC to bind to the plastic. The wells may be precoated with substances that enhance attachment of δPKC and/or that decrease the level of non-specific binding.

The plate is then incubated with a blocking solution (containing, for example bovine serum albumin) and then washed several times. A solution containing reporter-labelled (e.g., radiolabelled of fluorescently-tagged) peptide δV1-1 (SEQ ID NO:4) and, in the test wells, as opposed to the control wells, a test compound is added. Different wells may contain different test compounds or different concentrations of the same test compound. Each test compound at each concentration is typically run in duplicate and each assay is typically run with negative (wells with no test compound) as well as positive (wells where the "test compound" is unlabeled peptide) controls. The free peptide is then washed out, and the degree of binding in the wells is assessed.

A test compound is identified as active it if decreases the binding of the peptide, i.e., if its effect on the extend of binding is above a threshold level. More specifically, if the decrease in binding is a several-fold different between the control and experimental samples, the compound would be considered as having binding activity. Typically, a 2-fold or 4-fold threshold difference in binding between the test and control samples is sought.

Detection methods useful in such assays include antibody-based methods, direct detection of a reporter moiety incorporated into the peptide, such as a fluorescent label, and the like.

A variety of test compounds may be screened, including other peptides, macromolecules, small molecules, chemical and/or biological mixtures, fungal extracts, bacterial extracts or algal extracts. The compounds can be biological or synthetic in origin.

From the foregoing, it can be seen how various objects and features of the invention are met. New activator and inhibitor peptides of δPKC translocation and function were identified. The peptides can be delivered in vivo or ex vivo to achieve a functional inhibition or activation of δPKC. For example, delivery of the peptides to an intact heart via the coronary artery permits the peptides to act as a direct peptide modulator of protein-protein interactions intracellulary. It was also found that inhibition of δPKC by delivery of a δPKC antagonist reduces tissue damage due to an ischemic event. It is noteworthy that δPKC and εPKC (previously described in the art) exhibit an opposing effect in response to ischemia, yet activation of both isozymes leads to a similar form of cardiac hypertrophy. This was particularly unexpected, because both isozymes are activated by ischemia as well as by stimuli that lead to cardioprotection from ischemia (Gray, M. O. et al., Chen, C.-H. et al). δPKC and εPKC are opposing forces and a balance between these opposing forces likely determines the outcome to the ischemic insult, where protection occurs when activation of εPKC exceeds that of δPKC. During a long ischemic period, there may be an advantage to induce cell death, which will result from a time-dependent increase in the activity of δPKC relative to that of εPKC. In that way, the limited amounts of oxygen, glucose and other nutrients could be used by the remaining, less damaged, cells, ultimately leading to an improved outcome to the organ.

V. EXAMPLES

The following examples further illustrate the invention described herein and are in no way intended to limit the scope of the invention.

Example 1

Activity of δV1-1, δV1-2 and ψδRACK

A. Peptide Preparation

δV1-1 (SEQ ID NO:4) and ψδRACK (SEQ ID NO:6) were synthesized and purified (>95%) at the Stanford Protein and Nucleic Acid Facility. The peptides were modified with a carrier peptide by cross-linking via an N-terminal Cys-Cys bond to the *Drosophila* Antennapedia homeodomain (SEQ ID NO:8; Théodore, L., et al.; Johnson, J. A. et al., 1996b); In some studies not reported here, the peptides were lined to Tat-derived peptide (SEQ ID NO:9).

B. Peptide Delivery Into Cells

Primary cardiac myocyte cell cultures (90-95% pure) were prepared from newborn rats (Gray, M. O. et al.; Disatnik M.-H. et al.). The peptides δV1-1 and ψδRACK were introduced into cells at an applied concentration of 500 nM in the presence and absence of phorbol 12-myristate 13-acetate (PMA) at concentrations of 3 nm and 10 nm, respectively, for 10-20 minutes. In a third set of cells, the peptide δV1-1 was applied at a concentration of 500 nM in the presence and absence of 500 nM ψδRACK.

Translocation of δPKC isozyme was assessed by using δPKC isozyme-specific antibodies in Western blot analysis (Santa Cruz Biotechnology). Western blot analysis of cytosolic and particulate fractions of treated cells was carried out as described by Johnson, J. A., et al., *Circ. Res.* 76:654 (1995). Subcellular localization of dPKC isozymes was assessed by chemiluminescence of blots probed with anti-δPKC, anti-αPKC and anti-δPKC antibodies. Amounts of PKC isozymes in each fraction was quantitated using a scanner and translocation is expressed as the amount of isozymes in the particulate fraction over the amount of isozymes in non-treated cells. Changes in translocation of δPKC isozyme were also determined by immunofluoresence study of treated and fixed cells (Gray et al., 1997). Translocation was determined by counting over 100 cells/treatment in a blinded fashion. The results are shown in FIG. 2A-2B, FIGS. 3A-3B and FIGS. 4A-4B.

Example 2

Peptide Administration to Isolated Cardiac Myocytes

The peptides δV1-1 and WRACK were prepared as described in Example 1.

Adult male Wistar rat cardiomyocytes were prepared on a Langendorff apparatus (van der Heide, R. S. et al., *J. Mol. Cardiol.* 22:165 (1990)) by collagenase treatment (Armstrong, S. et al., *Cardiovasc. Res.*, 28:72 (1994)). The cells were treated with δV1-1 at concentrations of 10 nM, 100 nM, 500 nM, and 1 μM in the presence or absence of 1 μM ψδRACK. βPKC-selective activator was used as a control.

For stimulated ischemia, adult myocytes treated in microcentrifuge tubes with δV1-1 and/or ψδRACK peptides conjugated to the carrier were washed twice with degassed glucose-free incubation buffer and pelleted. On top of a minimal amount of buffer, the cell pellets were overlaid with either a micro-balloon (Sig Manufacturing, Montezuma, Iowa) or with degassed buffer satured with nitrogen, and sealed with an airtight top. Tubes were then incubated at 37 C for either 180 minutes or 90 minutes.

Cell damage was assessed by an osmotic fragility test by measuring the uptake of trypan blue, added in a hypotonic (85 mosM) solution. The results are shown in FIGS. 5A-5B. Similar results were also obtained by using a live-dead kit (Molecular Probes) or measuring the release of lactose dehydrogenase to the medium using a kit (Sigma) as previously described (Chen, et al., 1999; Gray et al., 1997; Mackay, K., et al. *J. Biol. Chem.*, 274:6272-6279 (1999)).

Example 3

Ex Vivo Peptide Administration to Whole Hearts and Effect on Cell Damage

Adult, male rats were anesthetized with i.p. avertin, and their hearts were rapidly removed and cannulated via the aorta for perfusion as described in the art (Colbert, M. C. et al, *J. Clin. Invest.* 100:1958 (1997)) using Langendorff set-up. Care was taken to have the hearts perfused within 90 seconds of removal. The hearts were perfused with oxygenated Krebs-Henseleit solution comprised of, in nmol/L, NaCl 120; KCl 5.8; NaHCO$_3$ 25; NaH$_2$O$_4$ 1.2; MgSO$_4$ 1.2; CaCl$_2$ 1.0; and dextrose 10, pH 7.4 at 37 C.

After a 10-20 minute equilibration period, the hearts were perfused with δV1-1 peptide (SEQ ID NO:4) or with ψδRACK peptide (SEQ ID NO:6), prepared as described in Example 1 but conjugated to a Tat-derived peptide (Tat 47-57, SEQ ID NO:9), for 20 minutes. Perfusion was maintained at a constant flow of 10 mL/min with Krebs-Hanseleit solution containing 0.5 μM of the appropriate peptide. The Langendorff method employed used retrograde flow from the ventricle to the aorta and into the coronary arteries, bypassing the pulmonary arteries.

To induce global ischemia, flow was interrupted for 30 minutes. After the ischemic event, the hearts were re-perfused for 30-60 minutes. During reperfusion, ischemia-induced cell damage was determined by measuring the activity of creatine phosphokinase (CPK) (absorbance at 520 nm) in the perfusate using a Sigma kit. As controls, some ex vivo hearts were left untreated, or maintained under normoxia conditions, or treated with the Tat-carrier peptide alone, or treated with Tat-carrier peptide conjugated to a scrambled δV1-1 peptide. The results are shown in FIGS. 6A-6B.

Example 4

Ex Vivo Peptide Administration to Whole Hearts and Effect on Functional Recovery Rat hearts were isolated as described in Example 3. The left ventricular pressure and its real-time derivative (dP/dt) were monitored via a latex balloon placed in the ventricular cavity and at a constant heart rate by pacing (3.3 Hz) and at a constant coronary flow (10 ml/min.). The hearts were subjected to 20 minutes of ischemia and 30 minutes of re-perfusion. During the first 20 minutes of reperfusion, 500 nM of δV1-1 or vehicle control was delivered. The results are shown in FIGS. 7A-7B.

Example 5

In Vivo Administration of δV1-1 After Ischemia

Adult female pigs, 35-40 kg in weight, were anesthetized and a catheter was introduced through the carotid artery into the heart. Using conventional intervention cardiology techniques, a wire was placed through a catheter and into the left anterior descending artery. A balloon was run over this wire to a site of occlusion where it was then inflated to block blood flow for 30 minutes. During the last 10 minutes of the 30-minute occlusion, either a control comprised of the carrier peptide alone or δV1-1 peptide (conjugated to a carrier Tat peptide as described in Example 3 was delivered by slow diffusion (1 mL/min) directly downstream of the occlusion. Approximately 20 kg of δV1-1 peptide (~400 ng per kg body weight) was administered.

After 30 minutes of occlusion, the balloon was removed and pigs were left to recover from surgery. Five days later, the pigs were euthanized and hearts were harvested. After heart removal, the LAD was occluded. With the occlusion in place, Evans Blue dye, which stains all areas not at risk of infarct in blue while leaving all areas with no access to blood flow red, was infused. Hearts were then cut into slices and stained with a tetrazolium red dye which stains all live areas red and infarcted dead tissue in white. Each heart had multiple tissue slices with distinctive areas marking the area at risk for ischemia and the infarcted area. From this the percent infarct per area at risk for each slice and for the entire heart was determined. The results are shown in FIGS. 9A-9C.

Example 6

In Vivo Administration of δV1-1 to Rats for Stroke Damage Protection

A. Cerebral Ischemia Model

Adult male Sprague-Dawley rats weighing between 280-320 g were used. Animals were maintained under isofluorane anesthesia during all surgical procedures. Physiological parameters were monitored and maintained in the normal range. Rectal temperature was also measured. At the completion of the experiment, the animals were euthanized with a barbiturate overdose and prepared for histological analysis.

B. Focal Model

Ischemia was induced using an occluding intraluminal suture. An uncoated 30 mm long segment of 3-0 nylon monofilament suture with the tip rounded by flame was inserted into the stump of the common carotid artery and advanced into the internal carotid artery approximately 19-20 mm from the bifurcation in order to occlude the ostium of the middle cerebral artery. Sham control animals underwent similar anesthesia and surgical manipulation, but did not experience ischemia. At the end of a 2 hour ischemic period, the suture was removed and the animal allowed to recover. Brains were harvested after 24 hrs of reperfusion.

C. Peptide Delivery

δV1-1 (SEQ ID NO:4) conjugated to Tat peptide (0.05 mL, SEQ ID NO:8) or Tat carrier control peptide (50 μL of 10 μM solution in saline) were injected into the carotid artery either immediately before or before and after the 2 hours occlusion. The final blood concentration of δV1-1 was 1 μM.

D. Histology

Animals were perfused with heparinized saline and brains removed and sectioned into 2 mm thick slices. To assess ischemic injury, brain sections were stained with cresyl violet or with triphenyl tetrazolium chloride, a live tissue stain to indicate the regions of infarct. Areas of infarction (white) were then measured using an image analysis system previously described (Yenari, M. A. et al., *Brain Res.,* 739:36-45 (1998), 1998; Maier, C. et al., *Stroke* 29:2171-2180 (1998)). The results are shown in FIGS. 11A-11B.

Although the invention has been described with respect to particular embodiments, it will be apparent to those skilled in the art that various changes and modifications can be made without departing from the invention.

The invention claimed is:

1. A method for reducing central nervous system tissue or cell damage in a human subject due to ischemic stroke, comprising
administering to said subject a conjugate comprising (a) a peptide comprising the amino acid sequence of SEQ ID NO: 4, and (b) a transport moiety effective to facilitate transport across a cell membrane, wherein said peptide and transport moiety are linked, and wherein said administering is effective to reduce central nervous system tissue or cell damage due to ischemic stroke.

2. The method of claim 1, wherein said peptide consists of the amino acid sequence of SEQ ID NO:4.

3. A method for reducing central nervous system tissue or cell damage in a human subject due to ischemic stroke, comprising
administering to said subject a conjugate comprising (a) a first peptide comprising the amino acid sequence of SEQ ID NO: 4, and (b) a second peptide comprising the amino acid sequence of SEQ ID NO: 9, wherein said first and second peptides are cross-linked via a disulfide bond, and wherein said administering is effective to reduce central nervous system tissue or cell damage due to ischemic stroke.

4. The method of claim 3, wherein said first peptide consists of the amino acid sequence of SEQ ID NO:4 and a terminal cysteine.

5. A method for reducing central nervous system tissue or cell damage in a human subject due to ischemic stroke, comprising
administering to said subject a conjugate comprising (a) a first peptide consisting of the amino acid sequence of SEQ ID NO: 4 and a first terminal cysteine, and (b) a second peptide consisting of the amino acid sequence of SEQ ID NO: 9 and a second terminal cysteine, wherein the first and second peptides are cross-linked via a disulfide bond between the first and second terminal cysteine, and wherein said administering is effective to reduce central nervous system tissue or cell damage due to ischemic stroke.

6. A method for reducing central nervous system tissue or cell damage in a human subject due to ischemic stroke, comprising
administering to said subject a composition comprising a conjugate and a carrier or encapsulant, wherein said conjugate comprises (a) a peptide comprising the amino acid sequence of SEQ ID NO: 4, and (b) a transport moiety effective to facilitate transport across a cell membrane, wherein said peptide and transport moiety are linked, and wherein said administering is effective to reduce central nervous system tissue or cell damage due to ischemic stroke.

7. The method of claim 6, wherein said peptide consists of the amino acid sequence of SEQ ID NO:4.

8. A method for reducing central nervous system tissue or cell damage in a human subject due to ischemic stroke, comprising
administering to said subject a composition comprising a conjugate and a carrier or encapsulant, wherein said conjugate comprises (a) a first peptide comprising the amino acid sequence of SEQ ID NO: 4, and (b) a second peptide comprising the amino acid sequence of SEQ ID NO: 9, wherein the first and second peptides are cross-linked via a disulfide bond, and wherein said administering is effective to reduce central nervous system tissue or cell damage due to ischemic stroke.

9. The method of claim 8 wherein said first peptide consists of the amino acid sequence of SEQ ID NO:4 and a terminal cysteine.

10. A method for reducing central nervous system tissue or cell damage in a human subject due to ischemic stroke, comprising
administering to said subject a composition comprising a conjugate and a carrier or encapsulant, wherein said conjugate comprises (a) a first peptide consisting of the amino acid sequence of SEQ ID NO: 4 and a first terminal cysteine; and (b) a second peptide consisting of the amino acid sequence of SEQ ID NO: 9 and a second terminal cysteine, wherein the first and second peptides are cross-linked via a disulfide bond between the first and second terminal cysteine, and wherein said administering is effective to reduce central nervous system tissue or cell damage due to ischemic stroke.

11. The method of any one of claims 1-10, wherein said administering comprises intravenously administering.

12. The method of any one of claims 1-10, wherein said administering occurs prior to said stroke.

13. The method of any one of claims 1-10, wherein said administering occurs during said stroke.

14. The method of any one of claims 1-10, wherein said administering occurs after said stroke.

* * * * *

UNITED STATES PATENT AND TRADEMARK OFFICE
CERTIFICATE OF CORRECTION

Page 1 of 1

| | |
|---|---|
| PATENT NO. | : 7,915,219 B2 |
| APPLICATION NO. | : 11/838732 |
| DATED | : March 29, 2011 |
| INVENTOR(S) | : Daria D. Mochly-Rosen and Leon E. Chen |

It is certified that error appears in the above-identified patent and that said Letters Patent is hereby corrected as shown below:

On column 1, Line 22: Change "This work was supported in part by The National Institutes of Health Grant HL52141. Accordingly the United States government may have certain rights in this invention".

to --This invention was made with Government support under contract HL052141 awarded by the National Institutes of Health. The Government has certain rights in this invention--.

Signed and Sealed this
Twenty-eighth Day of June, 2011

David J. Kappos
*Director of the United States Patent and Trademark Office*